_(12)_ United States Patent
Turki et al.

(10) Patent No.: US 11,597,907 B2
(45) Date of Patent: *Mar. 7, 2023

(54) **BIOMASS GROWTH COMPOSITION CONTAINING *HAEMATOCOCCUS* SP. STRAIN**

(71) Applicant: King Abdulaziz University, Jeddah (SA)

(72) Inventors: Adnan Jaman Turki, Jeddah (SA); Md. Abu Affan, Jeddah (SA); Salim Marzoog Al-Harbi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/227,762

(22) Filed: Apr. 12, 2021

(65) Prior Publication Data
US 2022/0177830 A1    Jun. 9, 2022

Related U.S. Application Data

(63) Continuation of application No. 17/113,754, filed on Dec. 7, 2020.

(51) Int. Cl.
| | |
|---|---|
| *C12N 1/12* | (2006.01) |
| *C12N 5/00* | (2006.01) |
| *C12R 1/89* | (2006.01) |

(52) U.S. Cl.
CPC ............. *C12N 1/12* (2013.01); *C12N 5/0018* (2013.01); *C12N 1/125* (2021.05); *C12R 2001/89* (2021.05)

(58) Field of Classification Search
None
See application file for complete search history.

(56) References Cited

U.S. PATENT DOCUMENTS

2014/0242676 A1    8/2014    Abdel-Fattah et al.

FOREIGN PATENT DOCUMENTS

| IN | 192839 B | 5/2004 | |
|---|---|---|---|
| KR | 10-1298942 B1 | 8/2013 | |
| WO | WO 2014/142423 A1 | 9/2014 | |
| WO | WO 2014/142540 A1 | 9/2014 | |
| WO | WO-2014142423 A1 * | 9/2014 | ............... C12P 1/00 |

OTHER PUBLICATIONS

Choi, Yoon Young; et al; "Development of large-scale and economic pH control system for outdoor cultivation of microalgae Haematococcus pluvialis using industrial flue gas" Bioresource Technology, 244, 1235-1244, 2017 (Year: 2017).*

Hu, Yukun; Yan, Jinyue; "Characterization of flue gas in oxy-coal combustion processes for CO2 capture" Applied Energy, 90, 113-121, 2012 (Year: 2012).*

Goksan, Tolga; et al; "Growth Characteristics of the Alga Haematococcus pluvialis Flotow as Affected by Nitrogen Source, Vitamin, Light and Aeration" Turkish Journal of Fisheries and Aquatic Sciences, 11, 377-383, 2011 (Year: 2011).*

Cheng, Jun; et al; "Gradient domestication of Haematococcus pluvialis mutant with 15% CO2 to promote biomass growth and astaxanthin yield" Bioresource Technology, 216, 340-344, 2016 (Year: 2016).*

Ravi Sarada, et al., "Influence of stress on astaxanthin production in *Haematococcus pluvialis* grown under different culture conditions", Process Biochemistry, vol. 37, Issue 6, 2002, pp. 623-627.

P. Bubrick, "Production of astaxanthin from *Haematococcus*", Bioresource Technology, vol. 38, Issues 2-3, 1991, pp. 237-239 (Abstract only).

* cited by examiner

*Primary Examiner* — David W Berke-Schlessel
(74) *Attorney, Agent, or Firm* — Oblon, McClelland, Maier & Neustadt, L.L.P.

(57) ABSTRACT

The invention is directed to *Haematococcus* sp. KAU-01 as well as to a culture medium for *Haematococcus* sp. KAU-01, and to methods for using this strain to process environmental pollutants such as gases generated by coal-fired plants.

14 Claims, 15 Drawing Sheets

FIG. 8A
FIG. 8B
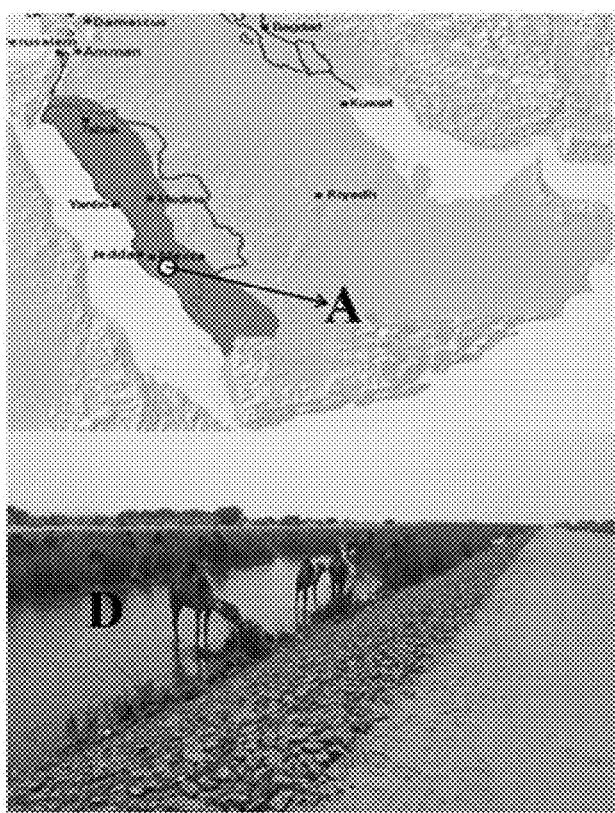
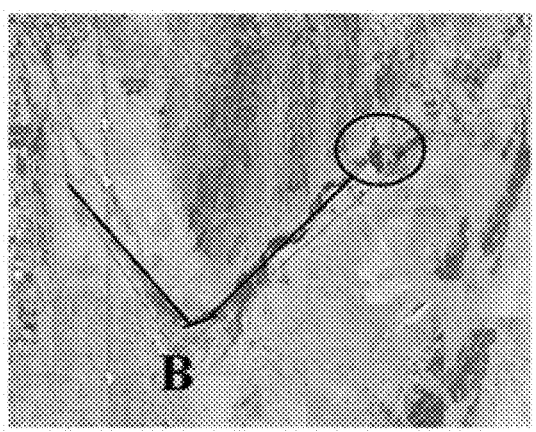
FIG. 8C
FIG. 8D

FIG. 9
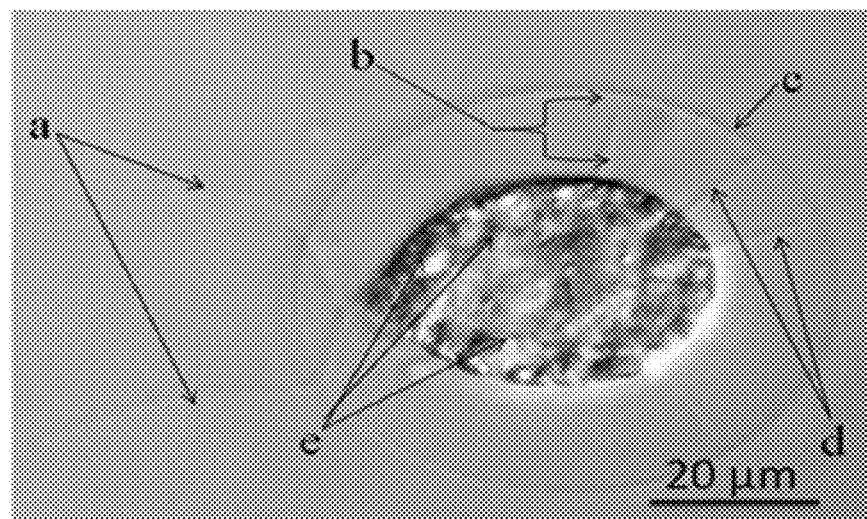
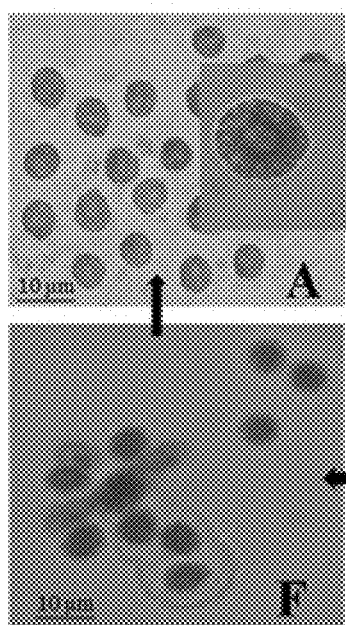
FIG. 10A  FIG. 10B  FIG. 10C
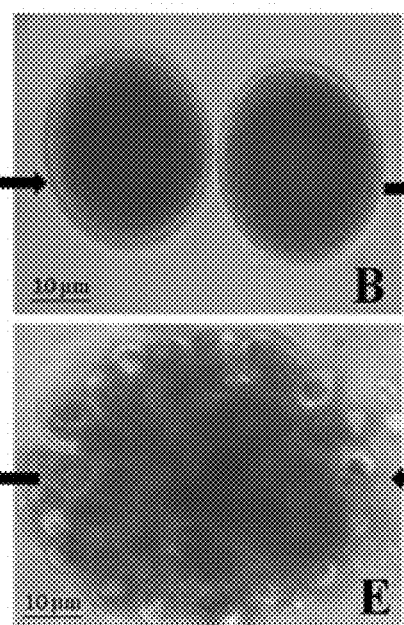
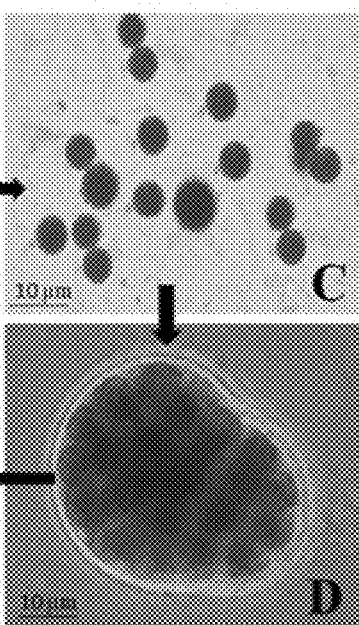
FIG. 10F  FIG. 10E  FIG. 10D

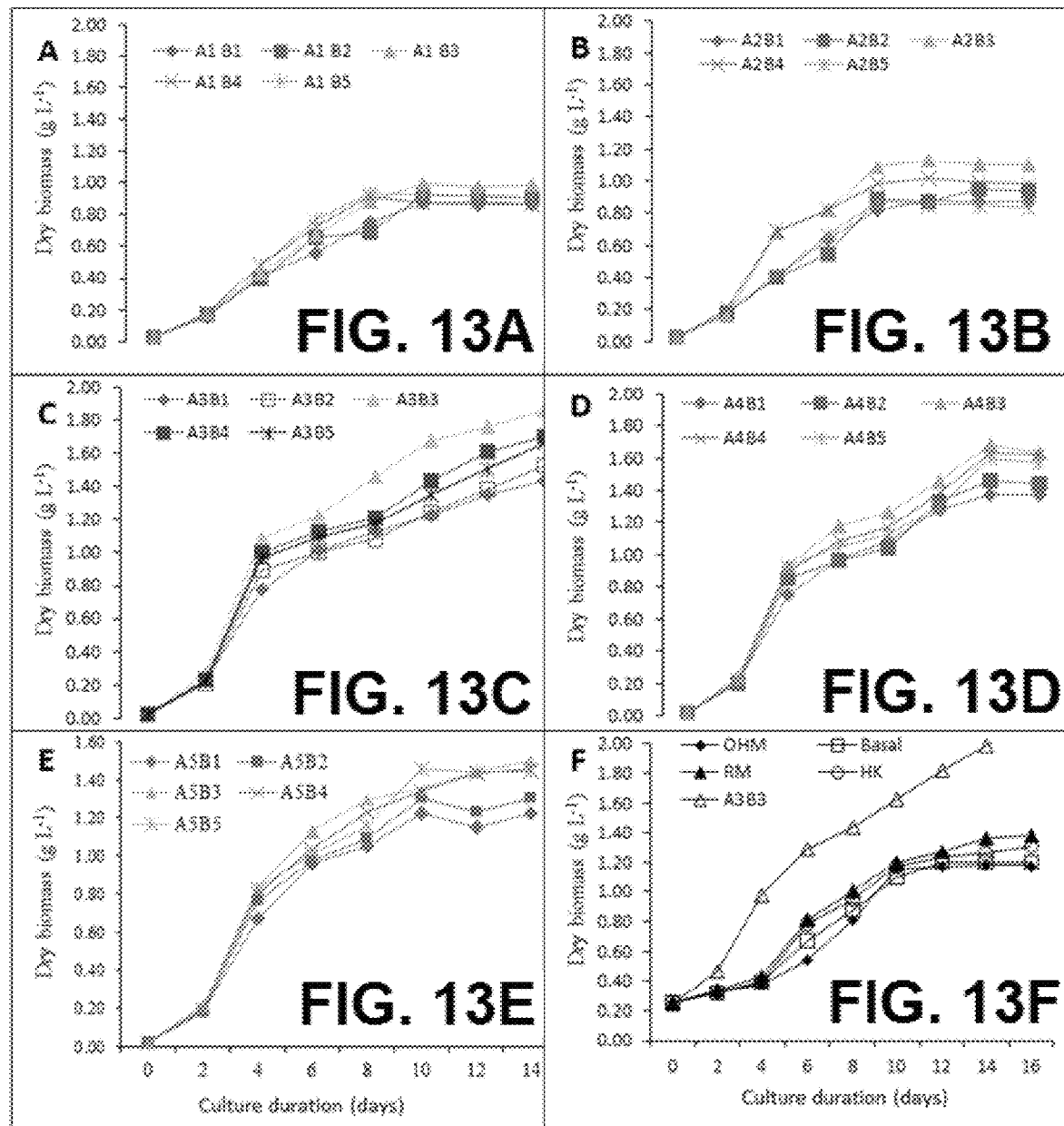

BIOMASS GROWTH COMPOSITION CONTAINING *HAEMATOCOCCUS* SP. STRAIN

CROSS-REFERENCE TO RELATED APPLICATION

This application is a continuation of U.S. application Ser. No. 17/113,754, filed on Dec. 7, 2020, pending. This application is related to U.S. application Ser. No. 17/113,816, filed Dec. 7, 2020, entitled BIOFIXATION OF GREENHOUSE GAS BY MASS CULTURE OF *HAEMATOCOCCUS* SP. KAU-01 MICROALGA IN HIGH EFFICIENCY MEDIUM which is hereby incorporated by reference.

BACKGROUND

Field of the Invention

The invention pertains to algology and environmental science, especially to new microalgae strains that efficiently metabolize carbon dioxide and other greenhouse gases, such as flue gases produced by coal-fired power plants.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

DESCRIPTION OF RELATED ART

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

It is well known that carbon dioxide is an important greenhouse gases ("GHGs") which can persist in the atmosphere for a long time. Carbon dioxide concentrations in air are increasing due to combustion of coal, petroleum, natural gas, and other fuels to produce energy. The increased atmospheric concentration of carbon dioxide plays a major role in global climate change, global warming, ocean acidification and other malignant environmental problems. Average planetary surface temperatures correlate with increases in atmospheric carbon dioxide and can lead to alterations in precipitation patterns, rises in sea level, and accelerated glacial melting.

Coal-fired power plants release carbon dioxide and other flue and greenhouse gases into the environment. Biofixation has been proposed as one way to reduce the emissions of gas produced by combustion into the atmosphere. Carbon dioxide and other combustion gases can be used as feedstocks to culture microorganisms such as microalgae that fixing them in organic materials such as biodiesel fuels, animal feeds, aquaculture feeds, and other high-valued materials such as pigments and nutraceutical products including astaxanthin; Cheng, J., et al., *Gradient domestication of Haematococcus pluvialis mutant with 15% $CO_2$ to promote biomass growth and astaxanthin yield*, BIORESOUR. TECHNOL, 2016, 216, 340-344; Williams, P. J. et al., *Microalgae as biodiesel & biomass feedstocks: review & analysis of the biochemistry, energetics & economics*. ENERGY ENVIRON. SCI. 2010, 3: 554-590; and Zheng, Q., et al., *Energy efficient transfer of carbon dioxide from flue gases to microalga systems*. ENERGY ENVIRON. SCI, 2016, 9: 1074-1082. Consequently, it is of critical importance to design and formulate a simple, efficient and inexpensive process for incorporating carbon dioxide and other combustion gases, which are generated from stationary sources like coal-fired power plants, into biomass while simultaneously removing these gases from the environment.

Numerous proposals have been made to attempt to capture and remove carbon dioxide produced by fossil fuel combustion or from the atmosphere. These include using molecular sieves or solvents to physically and chemical absorb carbon dioxide. Other methods include low temperature or cryogenic separation of carbon dioxide from air or other gases. Once carbon dioxide has been captured or separated in has been proposed to transport in and store it in geological formations. However, these methods for capturing and storing carbon dioxide are logistically complicated and expensive. Moreover such methods create new environmental risks including groundwater contamination or acidification, or geological instability including earthquakes. Such methods also create a new risk of leakage of the chemically or physically captured or separated carbon dioxide back into the atmosphere. Physical or chemical adsorption or separation and storage of carbon dioxide also do not solve problems associated with other gaseous components of combustion gas mixtures such as CO, $NO_x$ and $SO_x$.

In view of the above, the biological capture and fixation of carbon dioxide and other combustion gases into more complex molecules using microorganisms such as microalgae could offer a simple, convenient and economical way to capture carbon dioxide and other combustion gases. However, significant work is required to identify microalgae strains, culture media, and culture conditions suitable for efficient biofixation of carbon dioxide and other combustion gases. This is because different microalgae strains have different biochemical properties and growth rates and because conventional media limit the rate at which a microorganism can fix carbon dioxide or other combustion gases.

There is a significant need for a way to fix carbon dioxide and other combustion gases into biomass, most preferably, valuable biomass such as natural pigments. However, many conventional strains of microbes which can fix carbon dioxide have slow growth rates or produce little or no biomass of significant value. For example, many strains of the microalgae *Haematococcus* which can produce astaxanthin or other valuable natural pigments have slow growth rates in conventional media. These slow growth rates both limit their ability to remove carbon dioxide and other combustion gases from the air as well as negatively impacting the value of biomass they produce.

In addition to fixing combustion gases into biomass, the microbial production of natural pigments such as astaxanthin could supply a growing commercial market for these compounds which include polyisoprenoids such as β-carotene, astaxanthin, and canthaxanthin. These pigments are receiving greater attention because they are often used in the food, nutrition, and cosmetics industries; Patricia Veiga-Crespoet et al., *Influence of culture conditions of Gordonia jacobaea MY-26 on canthaxanthin production*, INTERNATIONAL MICROBIOLOGY, 2005, 8, 1. These pigments may be used for aquaculture of in animal feeds such as poultry feed or in nutraceuticals. For example, astaxanthin is a derivative of beta-carotene that is used as a food additive and natural colorant to enhance the appearance of pale colored cultured fish and shellfish, such as salmonoid fish and shrimp. It has been reported to have anti-inflammatory, anticancer and immunomodulatory properties and to confer numerous other health benefits for humans.

*Haematococcus* sp. often contain a high cellular content of astaxanthin typically ranging above 4% of its dry weight; Lee, Y. K., et al., *Accumulation of astaxanthin in Haematococcus lacustris (Chlorophyta)*. JOURNAL OF PHYCOLOGY. 1992, 3003, 575-577; Torzillo et al., JOURNAL OF APPLIED PHYCOLOGY, 2003, 15: 127-136. The cost of the dried powder of *Haematococcus* sp. is about 500 to $1,500/kg depending on its beta carotenoid and astaxanthin content; the price of purified astaxanthin can range upwards from about $70,000/kg.

*Haematococcus* is found world widely and its natural habitats are characterized by their unstable temporary conditions, which occur in small rock pools, water holes, bird baths, and other small natural or artificial bodies of water. *Haematococcus* sp. are unicellular green microalga with two flagella. They exhibit two types of cell morphology depending on environmental conditions. Under optimal growth conditions the cells are green and vegetative, proliferative, and capable of actively swimming using their flagella. However, under unfavorable conditions, the green vegetative cells drastically increase in volume, cease to be motile, and enter a resting stage to form cyst.

The green vegetative cells of *Haematococcus* are primarily composed of carotenoids which can contain 75-80 wt. % lutein, 10-20 wt. % β-carotene, as well as violaxanthin, neoxanthin, zeaxanthin, and chlorophyll a and b; Shah, M. M. R., et al., *Astaxanthin-producing green microalga Haematococcus pluvialis: From single cell to high value commercial products*. FRONT. PLANT SCI. 2016, 7, 531.

Typically astaxanthin production from *Haematococcus* is achieved through a two-stage culture comprising a vegetative (green) stage and aplanospore (red) stage. However, vegetative cultivation of *Haematococcus* is problematic due to slow growth rates, low cell densities, and susceptibility to contamination. Arrest of the growth of *Haematococcus* has been attributed to various factors including the production of immotile cells at a pH above 9.0, which can occur when a culture generates significant amounts of ammonia; conversion of vegetative motile cells into cysts after 4-6 days in conventional media; and release of cellular debris and blockade of the *Haematococcus* outer membrane by cellular debris. Unfortunately, while *Haematococcus* sp. can produce valuable biomass they lack the growth rates necessary to efficiently metabolize large quantities of carbon dioxide such as that in combustion or flue gases from coal-fired plants.

While many efforts have been made to boost the production of biomass from microalgae by using different media formulations, different kinds of vitamins, variation of light intensity or by use of mixed cultures of different algae, none have resulted in significant increases in production of algal biomass. Further, while conventional fed-batch microalgae culture can provide nutrients to facilitate continued microalga growth, it does not remove chemical inhibitors of microalga growth, such as free fatty acids like EPA. This results in the cessation of growth of the microalgae cultured followed by its gradual deterioration.

Apart from free fatty acid inhibitors, other culture components can inhibit microalga growth including debris generated from aging cell walls and broken cells. The inventors found that these materials inhibit microalga growth by favoring the formation of large cell aggregates which sequester nutrients needed for active growth of *Haematococcus* and other microalgae and which diminish the ability of microalgae to adsorb light.

Other factors which impair or inhibit the growth of *Haematococcus* and the production of valuable biomass include the presence of contaminating microalgae or other microorganisms and sensitivity of microalgae to culture conditions, such as the source, intensity and light provided during cultivation In view of the problems described above, the inventors sought to formulate a culture medium and conditions for cultivation of select *Haematococcus* microalgae strains that avoid the problems with conventional *Haematococcus* strains, culture media and culture methods in order to enhance biofixation of combustion gases as well as yields of valuable biomass.

BRIEF SUMMARY OF THE INVENTION

In view of the limitations of conventional microalgae strains and those of conventional culture media and culture methods, the inventors selected and cultured in vitro a new strain of microalgae designated *Haematococcus* sp. KAU-01, formulated a new culture medium for this strain, and developed a new methods for mass culture for this strain that inhibit contamination by other microorganisms, removes inhibitors of microalgae growth, avoid undesired turbidity, and produce commercially valuable biomass using greenhouse gases and other products of combustion thereby removing these gases as environmental pollutants. This high passage number strain has become stable after several passages where more than 80% of the cells died and has subsequently been viably stored. It has been designated *Haematococcus* sp., KAU-01. It may exhibit genetic and epigenetic changes compared to the original isolate due to repeated passage and selection in vitro.

In conjunction with the selection of the microalgae *Haematococcus* sp. KAU-01, the inventors developed a new culture medium containing a mixture of both micro- and macronutrients to cultivate this strain. This culture medium contains calcium nitrate in an amount that facilitates the growth and biomass production by *Haematococcus* sp. KAU-01 while avoiding undesirable turbidity in the medium especially at high pH.

Another approach developed and used by the inventors to increase the efficiency of microalgae biomass production is the use of a filter system to remove inhibitors of microalgae growth without removing viable cells. One example of such a system is one that uses a bag net filter having a 5 μm mesh size through which spent culture medium containing inhibitors is discharged without loss of microalgae cells, followed by the replacement of spent culture medium with fresh medium not containing the inhibitors or particulate matter.

To provide a simple and more economical process of culturing of *Haematococcus* sp. KAU-01, the inventors developed culture method that did not require sterilization of tap water or use of sterile distilled water. They found that contaminating microorganisms could be controlled during a bulk culture by acidifying culture water to a pH below 3.0 to kill microorganisms by acidic hydrolysis prior to adjusting the medium to a more neutral pH and inoculating *Haematococcus* sp. KAU-01. This step permits the use of unsterilized fresh or sea water and avoids the complexities and costs of autoclaving or filtering water prior to its use for mass or industrial-scale culture.

Embodiments of this technology include, but are not limited to the following.

One aspect of this technology is a Haematococcus sp. that is Haematococcus sp. KAU-01 submitted for deposit at the American Type Culture Collection (ATCC) on Feb. 13, 2022 under patent depository number P0088700 or an engineered variant thereof that has genomic or ribosomal DNA at least 99% identical to that of Haematococcus sp. KAU-01. Ribosomal DNA includes 18S and 26S rRNA gene sequence data.

In one embodiment, the *Haematococcus* sp. consists of *Haematococcus* sp. KAU-01, a subculture thereof, or a subculture that has been passaged in vitro 10, 20, 30, 40, 50 or more times. Preferably, *Haematococcus* sp. KAU-01 is passaged in AAHKAU medium.

In another embodiment, the *Haematococcus* sp consists of a genetically engineered variant of *Haematococcus* sp. KAU-01 that compared to the deposited strain of *Haematococcus* sp. KAU-01 that has been altered to have at least one mutation to its DNA and/or that has been transformed with an exogenous polynucleotide. These modifications include point mutations and other alterations in the DNA sequence of *Haematococcus* sp. KAU-01 or its chloroplasts.

Methods and vectors for genetic modification of *Haematococcus* sp. KAU-01 are known in the art and are incorporated by reference to Saei, A. A. et al., *Haematococcus as a promising cell factory to produce recombinant pharmaceutical proteins* MOLECULAR BIOLOGY REPORTS, 2012, 39, 9931-9939. In related embodiments, *Haematococcus* sp. KAU-01 may be used as a host cell for the recombinant expression of vaccine proteins, enzymes, and other valuable proteins.

*Haematococcus* sp. KAU-01 may be modified to increase its stability by reducing epigenetic changes in its genome. Methods for epigenetic stabilization are known and are incorporated by reference to J. E. Pais & R. Spreafico. *Avoiding epigenetic silencing of exogenous nucleic acid in algae*, US20200190485A1, 2020. Thus, one embodiment of the invention is directed to *Haematococcus* sp. KAU-01 that has been modified to by mutating or attenuating the methyltransferase (MTase) as well as other genes involved in epigenetic modification of *Haematococcus*. For example, one embodiment is directed to a mutant or modified *Haematococcus* sp. KAU-01 comprising a mutated or attenuated gene encoding a polypeptide having a CHG DNA methyltransferase activity, wherein the mutant or modified *Haematococcus* sp. KAU-01 has reduced CHG DNA methylation as compared to *Haematococcus* sp. KAU-01.

Methods for chloroplast modification are known in the art and are incorporated by reference to Gutiérrez, C. L., et al., *Chloroplast genetic tool for the green microalgae Haematococcus pluvialis* (Chlorophyceae, Volvocales), J. PHYCOLOGY, 2012, 48(4):976-983.

In another embodiment, the *Haematococcus* sp consists of an epigenetically modified or engineered variant of *Haematococcus* sp. KAU-01, Epigenetic modifications may be introduced by repeated passage and growth of *Haematococcus* sp. KAU-01 in vitro, such as passage or growth under stressful conditions, such as in nutrient depleted medium or at lower or higher temperatures than 25 to 30° C. such as at 15, 20 to <25° C. or >30, 35 to 40° C., in particular concentrations of specific nutrients or medium components, in medium exposed to combustion gases, under reduced or enhanced lighting compared to lighting conditions disclosed herein, under UV or chemical exposure, or cultivation at temperatures above or below room temperature or at high pH above 8, 9 or 10.

Another aspect of this technology is a method for producing biomass comprising culturing *Haematococcus* sp. in a culture medium in the presence of light, wherein the light may be present intermittently, periodically or continuously. In some embodiments, the light is natural, reflected, filtered, focused, or concentrated sunlight.

In other embodiments, the culture medium contains at least one material comprising a product obtained by combustion which can be incorporated into a gas, liquid or solid prior to incorporating it into the culture medium.

The material, such as a combustion or greenhouse gas, may be obtained by combustion of coal and in some embodiments is obtained by combustion of coal from or via a flue gas scrubber. This material usually comprises carbon dioxide but may also constitute carbon monoxide, a nitrogen oxide, a sulfur oxide, a volatile organic compound. In some embodiments, the material may comprise a heavy metal present in the material prior to incorporating it into the culture medium. Preferably, undesirable or toxic components like heavy metals are removed from the material prior to contacting it with a culture medium containing *Haematococcus* sp. KAU-01, In some embodiments of this method the *Haematococcus* sp. KAU-01 is cultured by a fed batch method. For example, culturing can comprise fed-batch culturing wherein each feeding of the batch comprises replacing from 5, 10, 20, 30, 40, 50 to >50% of a spent culture medium with fresh culture medium and, optionally, adjusting the pH before, during or after feeding to range from 6 to 8.

In a preferred embodiment of a method for cultivating *Haematococcus* sp. KAU-01 the culture medium comprises AAHKAU medium. This medium contains the following components given in mg/L and µl/L:

375.00 mg/L $NaNO_3$,
75.00 mg/L $KNO_3$,
25.00 mg/L $Ca(NO_3)_2$,
55.00 mg/L $Mg(NO_3)_2.6H_2O$,
10.00 mg/L $K_2SO_4$,
45.00 mg/L $K_2HPO_4$,
40.00 mg/L $KH_2PO_4$,
23.75 mg/L $MgSO_4.7H_2O$
1.76 mg/L urea,
65 µl/L $HNO_3$,
15 µl/L $H_3PO_4$;
3.50 mg/L $FeCl_3.6H_2O$,
1.00 mg/L $H_3BO_3$,
0.25 mg/L $Co(NO_3)_2.6H_2O$,
0.10 mg/L $K_2Cr_2O_7$,
0.10 mg/L $CuSO_4.5H_2O$,
0.25 mg/L $MnSO_4.H_2O$,
0.75 mg/L $ZnSO_4.6H_2O$,
0.25 mg/L $(NH_4)6Mo_7O_{24}.4H2O$
1.00 mg/L $Na_2$-EDTA and
1.00 µl/L HCl; and a mixture of vitamins.

Typically the medium also contains a vitamin solution xxx

AAHKAU medium (1×) may be formulated from stock solutions A, B and C.

Stock solution A (1000×) contains:
375.00 g/L $NaNO_3$,
75.00 g/L $KNO_3$,
25.00 g/L $Ca(NO_3)_2$,
55.00 g/L $Mg(NO_3)_2.6H_2O$,
10.00 g/L $K_2SO_4$,
45.00 g/L $K_2HPO_4$,
40.00 g/L $KH_2PO_4$,
23.75 g/L $MgSO_4.7H_2O$ 1.76 g/L urea,
65 ml/L $HNO_3$, and
15 ml/L $H_3PO_4$;
Stock solution B (10,000×) contains:
35.00 g/L $FeCl_3.6H_2O$,
10.00 g/L $H_3BO_3$,
2.50 g/L $Co(NO_3)_2.6H_2O$,
1.00 g/L $K_2Cr_2O_7$,
1.00 g/L $CuSO_4.5H_2O$,
2.50 g/L $MnSO_4.H_2O$,
7.50 g/L $ZnSO_4.6H_2O$,
2.50 g/L $(NH_4)_6Mo_7O_{24}.4H_2O$
10.00 g/L $Na_2$-EDTA and
10.00 ml/L HCl.

Stock solution C (10,000×) typically contains 10 g/L thiamine, 0.03 g/L +D-biotin, and 0.001 g/L cyanocobalamin.

Typically, 1 ml of the 1000× stock solution 1, 0.1 ml of the 10,000× stock solution B, and 0.1 ml of the 10,000× stock solution B are diluted in water up to 1 L to form 1× AAHKAU medium. However, other amounts of these stock solutions may be used to produce mediums with a lower or higher concentration of particular components. The exact amounts of each ingredient in the stock solutions A, B and/or C or in the 1× AAHKAU preparation from stock solutions may vary by ±1, 2, 3, 4, 5, 6, 7, 8, 9 or 10%.

In the formulations above, in the Tables, and elsewhere herein, the concentrations of the ingredients forming a medium may vary by ±1, 2, 5, or 10% by weight or volume.

In a preferred embodiment of this method the *Haematococcus* sp. comprises, consists essentially of, or consists of *Haematococcus* sp. KAU-01, a subculture thereof, or a genetically or epigenetically modified variant thereof.

In some embodiments of this method, biomass that is produced by the *Haematococcus* culture is recovered by filtration, centrifugation and/or sedimentation.

BRIEF DESCRIPTION OF THE DRAWINGS

FIGS. 8A-8B. Maps of sample collection area for *Haematococcus* sp. KAU-01.

FIGS. 8C-8D. Terrain of sample collection area at Green Valley, Jeddah, the Kingdom of Saudi Arabia.

FIG. 9. Green vegetative cell with (a) two flagella, (b) trilaminar sheath, (c) cytoplasmic strands and (e) pyrenoids as observed under inverted light microscope.

FIGS. 10A-10F. Life cycle from green, vegetative motile form to non-motile aplanospore.

FIG. 10A: shows green, motile vegetative flagellated cells.

FIG. 10B shows large aplanospores with red astaxanthin at the center and spreading towards a circle and green chlorophyll a around peripheries.

FIG. 10C shows fully red color aplanospore.

FIGS. 10D and 10E depict asexual reproduction of aplanospore.

FIG. 10F shows daughter cell are coming out by breaking aplanospore cell wall with little astaxanthin.

FIGS. 13A-13F. Growth and dry biomass production of *Haematococcus* sp. KAU, culture in square design combinations of A and B stock solutions. See Tables 2, 3 and 4 below for media formulations for A1-A5 and B1-B5.

FIG. 13A. Dry biomass produced by culture in major nutrient concentrations A1 in combination with minor nutrient concentrations B1-B5.

FIG. 13B. Dry biomass produced by culture in major nutrient concentrations A2 in combination with minor nutrient concentrations B1-B5.

FIG. 13C. Dry biomass produced by culture in major nutrient concentrations A3 in combination with minor nutrient concentrations B1-B5. Combination A3B3 provided superior results compared to other A3 combinations.

FIG. 13D. Dry biomass produced by culture in major nutrient concentrations A4 in combination with minor nutrient concentrations B1-B5.

FIG. 13E. Dry biomass produced by culture in major nutrient concentrations A5 in combination with minor nutrient concentrations B1-B5.

FIG. 13F. Dry biomass produced by culture in major nutrient concentrations A3 in combination with minor nutrient concentration B3 ("A3B3") compared to conventional media OHM, RM, Basal and HK. Combination A3B3 provides superior results compared to all comparative media.

DETAILED DESCRIPTION OF THE INVENTION

Figure 1:
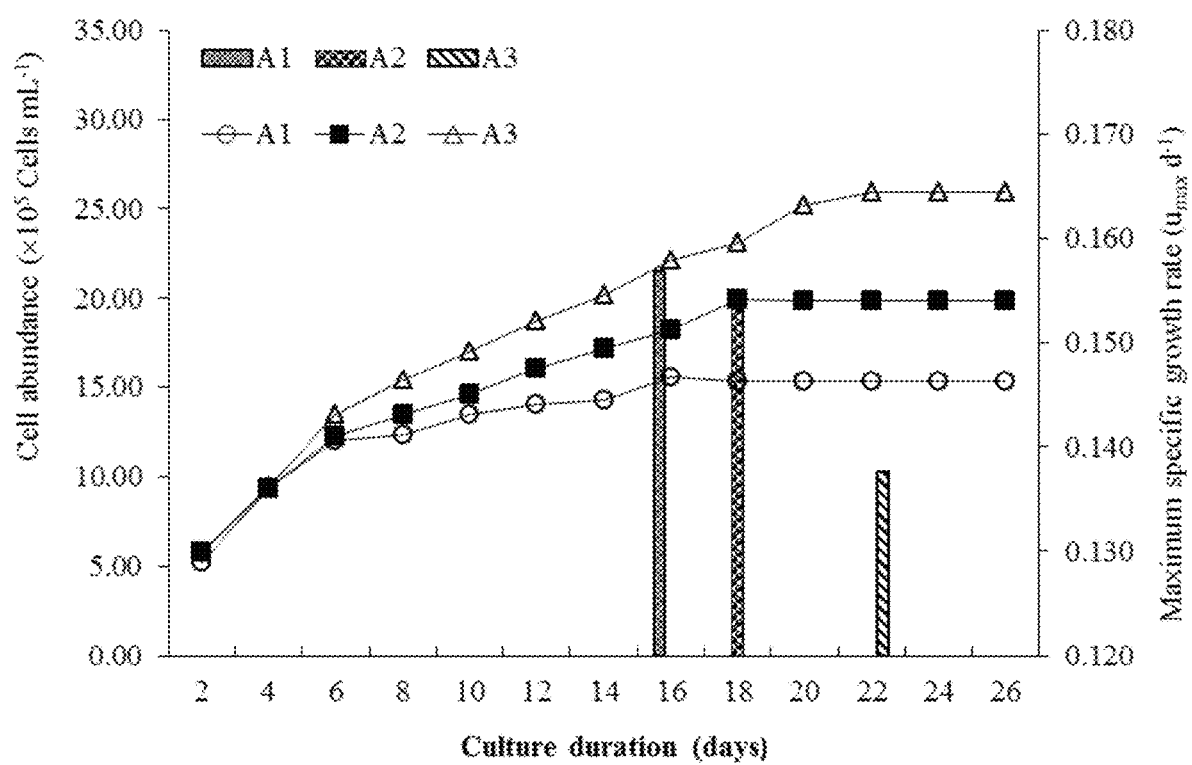
FIG. 1. Variation in maximum specific growth rate ($u_{max}$ $d^{-1}$) and growth curves with cell abundance (×$10^5$ cells $mL^{-1}$) of *Haematococcus* sp. KAU cultured in AAHKAU medium within 'A' culture group. A1: continuous aeration with normal air; A2: continuous aeration with normal air, pH was maintained at pH 7.5 by injecting amounts of stock solutions A and B; A3: continuous aeration with normal air, 20% media replacement on alternate days.

*Haematococcus* is a genus of algae in the family Haematococcaceae. The term *Haematococcus* sp. describes an unspecified species in the genus *Haematococcus* and *Haematococcus* sp. KAU-01 describes the particular deposited unspecified species isolated from a hot, tropical climate, cultivated or selected in vitro, and characterized by the inventors. In contrast to the native isolate, this strain can exhibit genetic or epigenetic changes that permit it to efficiently grow outside its natural environment, fix combustion gases, and produce valuable biomass. *Haematococcus* sp. KAU-01 (KAU#1) is a stable monostrain which has been deposited under the terms of the Budapest Treaty at the ATCC Patent Depository, 10801 University Boulevard, Manassas, Va. 20110 under Patent Deposit Number PTA-12727.

*Haematococcus* sp. KAU-01 was isolated away from other microalgae identified at Green Valley of Jeddah KSA including away from microalgae which belong to *Chlorophyta* such as *Pediastrum* sp., *Scenedesmus* sp., and *Volvox* sp. These other kinds of *Chlorophyta* differ from *Haematococcus* sp. KAU-01 as evident from their morphological characteristics. Based on its growth and metabolic properties, the inventors believe that significant phylogenetic differences distinguish *Haematococcus* sp. KAU-01 from other *Haematococcus* sp. such as *H. pluvialis, H. capensis, H. carocellus, H., lacustris,* and *H. zimbabwiensis.*

The parent isolated of the *Haematococcus* sp, which was later passaged and deposited as *Haematococcus* sp. KAU-01, was isolated from a natural sample using several steps. Initially, free swimming cells were collected using mouth sucking micro-pipetting and innoculated cultured in F/2 medium. Soon after inoculation, it was found that some cell walls were broken and the cellular materials were coming out resulting the death of the cells. Subsequently, the natural sample was filtered onto whatman (GF/F) which was kept at room temperature for about four days to dry. Thereafter, the whole filter paper was again sunk in the F/2 culture medium. Free swimming cells were again isolated by mouth sucking micropippetting.

Agar culture of the free swimming cells was done to get a mono-strain, the growth of which was then evaluated on several different culture media: BG11, MBG11, OHM, Basal, RM, HK, and MCM, see Table 1. Unfortunately, it was found that cell growth ceased after only 4-6 days when the free swimming cells were inoculated and cultured in these media. Therefore, it was decided to formulate a new culture medium for this species.

Several trial and error studies were conducted using novel media. Cells grown in these media were continuously observed under the microscope. Observations were made of cell division, cell movement, cyst formation, and regeneration from the cysts, as well as culture turbidity and sedimentation. As disclosed herein, a medium designated AAHKAU medium was developed using this process specially formulated for cultivating the isolated *Haematococcus* sp. KAU-01.

Microalgae including *Haematococcus* may be mutagenized by procedures known in the art including by exposure to mutagens such as UV light, ethyl methane sulphonate (EMS) and 1-methyl 3-nitro 1-nitrosoguanidine (NTG); Kamath, et al., BIORESOURCE TECHNOLOGY, 2008, 99, (18), 8667-8673 (incorporated by reference). Such methods may be used to mutate *Haematococcus* sp. KAU-01.

*Haematococcus* and other microalgae may be genetically engineered and transformed with exogenous polynucleotides by other methods known in the art; Sharon-Gojman, et al., ALGAL RESEARCH, 2015, 10, 8-15 or Steinbrenner, et al., APPL. ENVIRON. MICROBIOL. 2006, 72(12): 7477-7484 (both incorporated by reference). Such methods are used to transform or otherwise genetically modify *Haematococcus* sp., such as *Haematococcus* sp. KAU-01.

In some embodiments of the methods disclosed herein, a natural isolate or subculture thereof of a *Haematococcus* sp. is used. In other embodiments, *Haematococcus* sp. KAU-01 is further engineered and modified, mutated, or epigenetically or genetically engineered.

Modified variants of *Haematococcus* sp. KAU-01 may have one or more coding sequences, genes or polypeptides with alterations, such as deletions, substitutions or insertions of nucleotides or amino acid residues. Generally, related strains will have genomic DNA or one or more ribosomal DNA genes 95, 96, 97, 96, 99, 99.5, 99.9, <100 or 100% identical or similar to that of a parent or natural isolate of a *Haematococcus* sp., such as *Haematococcus* sp. KAU-01.

BLASTN may be used to identify a polynucleotide sequence having at least 70%, 75%, 80%, 85%, 87.5%, 90%, 92.5%, 95%, 97.5%, 98%, 99% or <100% sequence identity to a reference polynucleotide such as a polynucleotide of *Haematococcus* sp. KAU-01. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to hypertext transfer protocol secure://blast.ncbi.nlm.nih.gov/Blast.cgi?PROGRAM=blastn&PAGE_TYPE=BlastSearch&LINK_LOC=blasthome (last accessed Oct. 13, 2020).

A mutant or variant form of *Haematococcus* sp. KAU-01 may be characterized by expression of one or more mutant proteins that differ from a corresponding protein of *Haematococcus* sp. KAU-01 or by genetic or epigenetic modifications to its nucleic acids.

BLASTP can be used to identify an amino acid sequence having at least 70%, 75%, 80%, 85%, 87.5%, 90%, 92.5%, 95%, 97.5%, 98%, 99% or <100% sequence identity, or similarity to a reference amino acid, such as a mutant *Haematococcus* sp. KAU-01 amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: hypertext transfer protocol secure:// blast.ncbi.nlm.nih.gov/ Blast.cgi?PROGRAM=blastp&PAGE_TYPE=BlastSearch &LINK_LOC=blasthome (last accessed Oct. 13, 2020).

In some embodiments, *Haematococcus* sp. KAU-01 is further modified or mutated, for example, by chemical or radiological mutation or by genetic engineering and recombinant DNA techniques. A modified form of *Haematococcus* may have one or more epigenetic changes to its DNA, such as a variant methylation or hydroxymethylation pattern in its genomic DNA, a difference in histone methylation, or difference in microRNA expression, compared to an otherwise identical isolate. Epigenetic variants are those having a heritable phenotype change that does not involve alterations in its DNA sequence.

Such modifications may be made to improve growth or biomass production under particular culture conditions, to protect it from contamination by other microorganisms, for example, by making it resistant to one or more antibiotics, or to improve its functional properties such as its growth rate or ability to produce higher densities of biomass under particular culture conditions, its ability to form or not form a biofilm, its ability to adhere or not adhere to a substrate such as plastic, glass, ceramic, or metal, or its ability to absorb light within a specific range of wavelengths, or to boost its ability to produce valuable biological materials, such as fatty acids or astaxanthin or hydrogen (hypertext transfer protocol secure://newatlas.com/algae-hydrogen-production-boost-tau/45831/). Such a modified microalgae may also be mutated or engineered to prevent production of one or more of such biological materials that interfere with growth of the microalgae or production of biomass. Modifications include induction of auxotrophy for one or more molecules made by the unmodified strain or the incorporation of expression control sequences such as repressible promoters into the genome or episomes of the microalgae.

Greenhouse gases absorb and emit radiation within the thermal infrared range and include water vapor, carbon dioxide, methane, nitrous oxide, and ozone.

Flue gases. Flue gases are produced when natural gas, fuel oil, coal, wood, cellulose wastes (e.g., grass, palm fronds, paper, cardboard, etc.) or any other carbon based fuel is combusted in an industrial furnace, a steam generator in a fossil fuel power plant or other combustion sources. Typically, flue gases consist of mostly nitrogen (typically more than two-thirds) derived from the combustion of air, carbon dioxide ($CO_2$), and water vapor as well as excess oxygen which may be derived from the combustion air and contain small percentages of various of pollutants, such as matter like soot, carbon monoxide, nitrogen oxides, sulfur oxides, volatile organic compounds, and hydrocarbons; see *Fossil fuel combustion flue gases*, Milton R. Beychok, ENCYCLOPEDIA OF EARTH, 2012 (incorporated by reference). Volatile organic compounds includes those emitted by burning coal such as aldehydes (formaldehyde and acetaldehyde), aliphatic and aromatic hydrocarbons (toluene, xylenes, ethylbenzene and benzene) and chlorinated hydrocarbons (tetrachloroethene); see Garcia, et al., ATMOSPHERIC ENVIRONMENT. PART A. GENERAL TOPICS, 1992, 26(9), 1589-1597 (incorporated by reference).

In some embodiments, one or more flue or greenhouse gases or pollutants are adsorbed or dissolved into a growth medium for *Haematococcus* sp. KAU-01. For example, in some embodiments a culture medium is contacted with or infused with a mixture of air with 1, 2, 3, 4, 5, 6, 7, 8, 9, 10, 11, 12, 13, 14, 15, 16, 17, 18, 19, 20, 21, 22, 23, 24 or 25% (v/v) carbon dioxide or other greenhouse or flue gases. The medium may be contacted or infused with one or more gases at a temperature ranging from 0, 5, 10, 15, 20, 25 or 30° C. and/or at a pressure of 1 (14.7 psi), 1.1, 1.2, 1.3, 1.4, 1.5, 1.6, 1.7, 1.8, 1.9, 2, 2.5, 3 or more atmospheres. The resulting medium may contain microalgae or be added or fed to an ongoing culture of microalgae.

In one embodiment, coal power plant gases are taken from the coal power plant chimney with pressure in to a reserve tank, held to adjust the temperature to one similar to air temperature, and then the gases are supplied to a *Haematococcus* culture so that the culture medium has a pH ranging from about 7.0-8.0, preferably about pH 7.5, The gases themselves or other buffers may be used to adjust the culture medium pH.

Cooling and heating may be performed in a tank or other container equipped with refrigeration or heaters and infusion conducted in a pressurized tank or other container. Temperature and pressure sensors, pumps or regulators may be incorporated into the tank as well as conduits or valves for delivering the temperature controlled or infused medium to feed the microalgae.

Fed-batch culture is an operational technique in biotechnological processes where one or more nutrients (substrates) are fed (supplied) to a bioreactor during cultivation and in which the product(s) remain in the bioreactor until the end of the run. In some embodiments of the invention *Haematococcus* sp. KAU-01 is cultivated in a fed-batch culture which provides fresh nutrients for its growth and which removes spent medium containing growth inhibitors, metabolites, or cellular debris that inhibit production or accumulation of biomass. Nutrients may be supplied to the fed-batch culture constantly or at a particular rate, such as by exponential feeding that is tied to the number of cells in the culture. In some embodiments, this method will include fed-batch culture of *Haematococcus* sp. where each feeding involves replacing or adding (supplementing with) from 1, 2, 5, 10, 15, 20, 25, 30, 35, 40, 45, 50, 55, 60, 65, 70, 75, 80, 85, 90, 95 or 100% by volume of the spent culture medium with fresh culture medium. Culture medium may be replaced every 12, 24 or 48 hours (or any intermediate period). Advantageously, culture medium may be replaced every other day after an initial culture period of 1, 2, 3, 4, 5 or 6 days. The temperature may be adjusted to fall within the range of 15, 20, 25, to 30° C. and pH adjusted before, during or after feeding for example, by adding acid, base or a buffer to bring the culture pH to 5, 5.5, 6, 6.5, 6.6, 6.7, 6.8, 6.9, 7, 7.1, 7.2, 7.3, 7.4, 7.5 or 8 or any intermediate value within this range. In some embodiments, up to 5, 10, 20, 30, 40, 50, 60, 70, 80, 90, 95, <100 or 100% of EPA or cellular debris are removed or diluted below their initial concentration, for example, by filtration of spent medium and replacement with fresh medium not containing these contaminants.

The rate of microalgae growth may be controlled by adjusting the temperature or pH of the culture or by reducing or increasing one or more nutrients or growth substrates, including an amount of one or more flue gases, for the microalgae.

In some embodiments, following fed-batch culture, the microalgae are harvested by sedimentation, filtration, or centrifugation. Microalgae may be harvested at one or more of their life cycle stages include during vegetative cell growth, encystment, maturation or germination.

Harvested microalgae may be used to make biofuel, nutraceuticals such as omega three fatty acids, glycoproteins, pigments or astaxanthin, or as animal or aquaculture feeds. Biological products made by microalga such as Haematococcus include beta-carotene, astaxanthin, canthaxanthin, lutein, other polyisoprenoids, EPA and other fatty acids. These may be harvested or recovered at a point in the alga lifecycle where they are maximally expressed or at a point where their purity is high at a time when little degradation or chemical transformation of the desired product has occurred, or when it is easy to isolate them from other algae components, for example, beta-carotene and lutein may be harvested when an algae is in a green vegetative state and astaxanthin from red cysts.

Bioreactor. Typically a bioreactor will include a container, such as a tank and a light source, where the tank contains a culture medium and dispersed algal cells such as Haematococcus sp. KAU-01 cells. The algal cell culture may have a concentration of greater than 0.05, 0.1, 0.2, 0.3, 0.4, 0.5, 0.6, 0.7, 0.8, 0.9, 1.0, 2.0 or >2.0 g/l in the culture medium.

It may have a paddle or other kind of agitator or mixer to keep the cells in suspension. Representative bioreactors or culture systems include circulating open pond, open racing pond, bubble column, airlift reactor, annular reactor, stirred tank reactor, flat panel (plate) reactor, hemispherical biodome, or simple horizontal tumbular reactor any of which may accommodate exposure of the algae to light by providing direct light exposure or exposure to light through a transparent or translucent or illuminated panel or container. A bioreactor may contain one or more mixing devices including, but not limited to, paddlewheels, gas sparging, and mechanical stirrers, to help expose cells to illumination and prevent them from settling to the bottom of a bioreactor. Bioreactors may include inlets (for fresh medium components) or outlets (to let out spent medium components or to recover algae). In some embodiments, the inlets and outlets are valved to regulate the flow of components. A bioreactor may also be equipped with filters or other separation devices that retain algae and pass spent culture medium components as well as cellular debris out of the culture medium.

A photobioreactor (PBR) is a bioreactor which incorporates a light source and may be used to cultivate Haematococcus sp. KAU-01 cells. Virtually any translucent container may be called a PBR and in some embodiments the PBR is a tank, a polyethylene or other clear or translucent plastic sleeve or gag or clear or translucent tubes, such as glass or plastic tubes. This term typically describes a closed system as opposed to an open tank or pond. A closed PBR system generally provides all the nutrients and micronutrients necessary for algae growth. A PBR can operate in "batch mode", which involves restocking the reactor after each harvest, but it is also possible to grow and harvest continuously. Continuous operation requires precise control of all elements to prevent immediate collapse. The grower typically provides sterilized water, nutrients, air, and carbon dioxide or other greenhouse or flue gases at a predetermined rate. Algae grown in the log phase is generally of higher nutrient content or better at removing or remediating flue or greenhouse gases than old senescent algae. In some embodiments of the invention, Haematococcus sp. KAU-01 cells are grown in a photoreactor using procedures and/or equipment that permit removal of growth inhibitory substances. In other embodiments, Haematococcus sp. KAU-01 may be grown under condition where EPA and cellular debris are continuously removed, for example, by growing it in flat transparent porous bags that retain viable Haematococcus sp. KAU-01 but permit outward diffusion of EPA and cellular debris or that permit sedimentation of cellular debris. These porous bags may be continuously, periodically or intermittently supplied with fresh culture medium.

Algal culture is the culturing of algae in ponds or other resources. Other modes of algae culture are described by and incorporated by reference to Borowitzka, Commercial production of microalgae: ponds, tanks, and fermenters, PROGRESS IN INDUSTRIAL MICROBIOLOGY, 1999, 35, 313-321. In some embodiments of the invention, Haematococcus sp. KAU-01 cells are grown in algal culture using procedures and/or equipment that permit removal of growth inhibitory substances.

Filtration. Spent medium which may contain growth inhibitory substances is typically removed by filtration through one or more filters that retain viable Haematococcus sp. KAU-01 cells, but which permit passage of growth inhibitory substances such as eicosapentaenoic acid (EPA) and cellular debris. These cells may range in particle size from about 5 to 25 microns and some representative filter mesh sizes range from about 1, 2, 3, 4, 5, 6, 7, 8, 9, 10, 11, 12, 13, 14, 15, 16, 17, 18, 19, 20, 21, 22, 23, 24 or 25 microns. As shown herein a filter bag or phytoplankton net mesh size of about 5 or 10 microns is suitable for retaining viable Haematococcus sp. KAU-01 cells. Other conventional or commercially available algae filters or scrubbers may be used. In some embodiments, other separation modes may be used including centrifugation or sedimentation to separate or partially separate viable cells from other culture components.

Other embodiments of the invention include, but are not limited to the following.

One embodiment of the invention is a wild type (unmodified), epigenetically modified, chemically modified, irradiated, mutated, or genetically engineered variant of Haematococcus sp. KAU-01 that has genomic DNA at least 70, 75, 80, 85, 90, 95, 96, 97, 98, 99, 99.5, 99.9, <100 or 100% identical to Haematococcus sp. KAU-01. A mutated or genetically engineered variant may contain 1, 5, 10, 20, 50, 100, 200, 500 or more deletions, substitutions or insertions of nucleotides into the genomic DNA or 1, 2, 3, 4, 5, 10, 20, 30, 40, 50, 100 or more deletions, substitutions or insertions into one or more proteins expressed by the microalgae. In some embodiments, this microalgae is a strain of Haematococcus other than Haematococcus sp. KAU-01 in admixture with other microalgae or microorganisms or as it may be found in nature. In some embodiments, the microalgae will be a genetically engineered variant of Haematococcus sp. KAU-01 that has been transformed with at least one exogenous polynucleotide, for example, by transformation with one or more plasmids or transposons that express antibiotic resistance or other selectable markers, which express enzymes which enhance microalgae growth or biomass production, or which contain control sequences that modulate (decrease, stabilize or enhance) microalgae growth or biomass production.

A *Haematococcus* sp. as isolated from nature may be further modified, for example, by chemical or radiological mutation or by genetic engineering such as by transformation with an exogenous polynucleotide sequence from a different type of organisms, such as a plant, microalgae, different type or strain of *Haematococcus*, animal, plant, fungus, or other eukaryotic or prokaryotic organisms, or by an artificial polynucleotide sequence. Exogenous polynucleotide sequences include detectable markers or sequences coding for chemical or antibiotic resistance, reporter, promoter, termination control sequence, and other expression control sequences, sequences coding biosynthetic enzymes or enhancing or otherwise modulating expression of astaxanthin, carotenoids or other chemical products produced by a microalgae. The sequence of an exogenous gene may be codon-modified to match it to that of a *Haematococcus* host cell.

Another embodiment of the invention is method for producing biomass comprising culturing in the presence of light and in a suitable medium *Haematococcus* sp. KAU-01 or a *Haematococcus* strain that has genomic DNA at least 80, 85, 90, 95, 96, 97, 98, 99, 99, 99.5, 99.9, <100 or 100% identical to *Haematococcus* sp. KAU-01 thereby producing biomass. In this method the light may be natural, reflected, filtered, focused or concentrated sunlight or, alternatively, artificial light or a mixture of natural and artificial light having a wavelength suitable for culture of *Haematococcus* sp. KAU-01. The wavelength of the used to cultivate microalgae is not particularly limited as long as it can be adsorbed and used by the microalgae to product biomass. Visible light having a wavelength ranging from 380, 400, 450, 500, 550, 600, 650, 700, 750 to 780 nm may be used. The amount or intensity of the light used to cultivate the microalgae is not particularly limited as long as it is sufficient for the microalgae to produce biomass. For example, respective photosynthetic photon flux densities (PPFD) in the vicinity of a light irradiation surface of the culture solution may range from 5 $\mu mol/m^2/s$ to 200 $\mu mol/m^2/s$, preferably 10 $\mu mol/m.^2/s$ to 100 $\mu mol/m^2/s$, and more preferably 20 $\mu mol/m^2/s$ to 70 $\mu mol/m^2/s$. Illumination of the microalgae may be continuous, periodic or intermittent. Preferred illumination periods range from 1, 2, 4, 6, 8, 10, 12, 14, 16, 18, 20, 22 or 24 hours and may be cyclic or non-cyclic. *Haematococcus* sp. KAU-01 is grown at a temperature suitable for its growth or production of biomass, for example, at a temperature ranging from 15, 16, 17, 18, 19, 20, 21, 22, 23, 24, 25, 26, 27, 28, 29, 30, 31, 32, 33, 34 or 35° C.

In some embodiments *Haematococcus* sp. KAU-01 is cultured outside, for example, in an outdoor circulating pool exposed to sunlight which contains 0.1, 0.2, 0.3, 0.4, 0.5, 0.6, 0.7, 0.8, 0.9, <1.0, 1.0, 1.1, 1.2, 1.3, 1.4, 1.50 or 2× of the culture medium ingredients described herein. Preferably, such culturing is performed at a pH ranging from 7.0-8.0, advantageously at an adjusted pH of 7.5.

One or more greenhouse or flue gases may be incorporated into or otherwise contacted with the medium in this method. These may be the direct products of combustion, such as coal, petroleum, natural gas, gasoline, diesel or other petrochemical combustion, or may be modified, mixed or processed prior to incorporation into a culture medium, for example, by adsorption into scrubber gases, liquids or solids to form a derivative or by admixture with air or other gases. Combustion gases include carbon dioxide, carbon monoxide, nitrogen oxide, sulfur oxides, and volatile organic compounds. Such gases in unpurified, partially purified or purified form may be pumped into or over or blown over the medium, or otherwise perfused or incorporated into the medium. In some embodiments products, such as those produced in a flue gas scrubber or catalytic converter, may be incorporated into the culture medium.

In some embodiments, one or more contaminants, such as heavy metal, carbon, ash, or other products of combustion may be removed from or separate from one or more of these combustion gases or their mixtures or derivatives prior to incorporation into a culture medium. Heavy metals include arsenic, antimony, lead, zinc, manganese, nickel, copper, and chromium. Reductions ranging from <5%, 10, 20, 30, 40, 50, 60, 70, 80, 90, 95, <100, or 100% of these metals may be made to lessen the impact of these metals on the growth of microalgae or the contamination of biomass produced by microalgae. Heavy metals may be captured and removed from combustion gases by methods known in the art include those described by Chen, et al., Science of the Total Environment 228 (1): 67-77 (1999, incorporated by reference) or Li, et al., Fuel 186:714-725 (2016, incorporated by reference).

In some embodiments, this method will include fed-batch culture of *Haematococcus* sp. KAU-01 where each feeding involves replacing from 1, 2, 5, 10, 15, 20, 25, 30, 35, 40, 45, 50, 55, 60, 65, 70, 75, 80, 85, 90, 95 or 100% by volume of the spent culture medium with fresh culture medium. The culture pH may be adjusted during, between or after a feeding, for example, by adding acid, base or a buffer to bring the culture pH to 5, 5.5, 6, 6.5, 6.6, 6.7, 6.8, 6.9, 7, 7.1, 7.2, 7.3, 7.4, 7.5 or 8 or any intermediate value within this range. Advantageously feedings are performed using AAHKAU medium or an AAHKAU-like medium and performed using *Haematococcus* sp. KAU-01 or a variant thereof whose genomic DNA is least 80, 85, 90, 95, 96, 97, 98, 99, 99.5 or <100% identical to *Haematococcus* sp. KAU-01. In some embodiments, not mutated or not-engineered *Haematococcus* sp. KAU-01 in other embodiments a modified, mutated or engineered variant of *Haematococcus* sp. KAU-01 that differs from the original isolate is cultivated.

In some embodiments, the biomass is recovered by filtration, centrifugation, and/or sedimentation of medium or other liquid containing the biomass. Biomass recovered from culture medium may be further washed, rinsed, dried, concentrated or otherwise processed, for example, to isolate a chemical component it contain such as a fatty acid, pigment, astaxanthin, or other nutraceutical product, to place it in a form for processing into biodiesel or other fuel, to place it in a usable form transport, or to put in into a form suitable as an animal or aquaculture feed.

In other embodiments, a species other than a *Haematococcus* sp. may be cultured in AAHKAU medium, such microorganisms include *Chlorophyta* such as *Pediastrum* sp. and Scencedesmus sp, Another embodiment of the invention is a composition comprising (i) an artificial culture medium and (ii) *Haematococcus* sp. KAU-01 or a mutated or genetically engineered variant of *Haematococcus* sp. KAU-01 that has genomic DNA at least 80, 85, 90, 95, 96, 97, 98, 99, 99.5, 99.9, <100 or 100% identical to *Haematococcus* sp. KAU-01. This composition may further include at least one greenhouse or gas resulting from the combustion of at least one hydrocarbon such as a flue gas from a coal-fired power plant. For example, the composition may contain one or more gases such as carbon dioxide generated by combustion or oxidation of fuel sources such as coal, petroleum, petrol (gas), diesel fuel, or alcohol or other fuels that produce carbon dioxide or greenhouse gases when oxidized.

Another embodiment of the invention is directed to a culture medium comprising major nutrients in the following ranges:

187.50 to 562.50 mg/L $NaNO_3$, 37.50 to 112.50 mg/L $KNO_3$, 12.50 to 37.50 mg/L $Ca(NO_3)_2$, 27.50 to 82.50 mg/L $Mg(NO_3)_2.6H_2O$, 22.50 to 67.50 mg/L $K_2HPO_4$, 20.00 to 60.00 mg/L $KH_2PO_4$, 5.00 to 15.00 mg/L $K_2SO_4$, 11.88 to 35.63 mg/L $MgSO_4.7H_2O$, 0.88 to 2.63 mg/L urea, 32.50 to 97.50 µl/L $HNO_3$, 7.50 to 22.50 µl/L $H_3PO_4$, and freshwater.

In typical embodiments, this culture medium further includes one or more of the following micronutrients $FeCl_3.6H_2O$, $H_3BO_3$, $Co(NO_3)_2.6H_2O$, $K_2Cr_2O_7$, $CuSO_4.5H_2O$, $MnSO_4.H_2O$, $ZnSO_4.6H_2O$, $Na_2$-EDTA and HCl. In one embodiment the micronutrients and vitamins fall within the following ranges 1.75 to 5.25 mg/L $FeCl_3.6H_2O$, 0.50 to 1.50 mg/L $H_3BO_3$, 0.13 to 0.38 mg/L $Co(NO_3)_2.6H_2O$, 0.05 to 0.15 mg/L $K_2Cr_2O_7$, 0.05 to 0.15 mg/L $CuSO_4.5H_2O$, 0.13 to 0.38 mg/L $MnSO_4.H_2O$, 0.38 to 1.13 mg/L $ZnSO_4.6H_2O$, 0.13 to 0.38 mg/L $(NH_4)_6Mo7O_{24}.4H_2O$, 0.5 to 1.5 mg/L $Na_2$-EDTA, and 0.5 to 1.5 µl/L HCl.

Preferably, the 1× medium further comprises 0.8 to 1.2 mg/L thiamine, 0.0024 to 0.0036 mg/L +D-biotin, and 0.00008 to 0.00012 mg/L cyanocobalamin.

The ranges herein include all intermediate subranges and values. For hydrated compounds, these amounts include the equivalent molar amounts of anhydrous or other hydrates of the same compound.

One example of an advantageous medium formulation is 1× AAHKAU medium solution as a *Haematococcus* sp., KAU-0/culture medium which contains:

375.00 mg/L $NaNO_3$,
75.00 mg/L $KNO_3$,
25.00 mg/L $Ca(NO_3)_2$,
55.00 mg/L $Mg(NO_3)_2.6H_2O$,
10.00 mg/L $K_2SO_4$,
45.00 mg/L $K_2HPO_4$,
40.00 mg/L $KH_2PO_4$,
23.75 mg/L $MgSO_4.7H_2O$,
1.75 mg/L urea,
65.00 µl/L $HNO_3$,
15.00 µl/L $H_3PO_4$;
3.50 mg/L $FeCl_3.6H_2O$,
1.00 mg/L $H_3BO_3$,
0.25 mg/L $Co(NO_3)_2.6H_2O$,
0.10 mg/L $K_2Cr_2O_7$,
0.10 mg/L $CuSO_4.5H_2O$,
0.25 mg/L $MnSO_4.H_2O$,
0.75 mg/L $ZnSO_4.6H_2O$,
0.25 mg/L $(NH_4)_6Mo7O_{24}.4H_2O$,
1.00 mg/L $Na_2$-EDTA,
1.00 µl/L HCl,
1.00 mg/L thiamine,
0.003 mg/L +D-biotin, and
0.0001 mg/L cyanocobalamin;
wherein each of said concentrations (mg/L) may vary ±0.5, 1, 1.5, 2, 2.5, 3, 3.5, 4, 4.5, 5, 5.5, 6.0, 7.5, 8, 8.5, 9, 9.5, or 10%.

In embodiments where greenhouse or combustion gases or by products are incorporated into a culture medium, these additional components may constitute at least a part of the one or more of the ingredients of AAHKAU medium or other culture medium disclosed herein; alternatively, they may be independent components and additives to a culture medium disclosed herein, for example, AAHKAU medium may be supplemented with carbon dioxide obtained from combustion and thus have a different composition than AAHKAU medium not supplemented with carbon dioxide or another greenhouse or combustion gas. Thus, gases which can come out of a mixture of flue gases can be used as components of AAHKAU medium.

Culture medium pH, salt content, osmolality, or temperature may be adjusted after addition of carbon dioxide or other combustion gases or their byproducts. In some embodiments, the culture medium, such as AAHKAU medium may be diluted to contain 10, 20, 30, 40, 50, 60, 70, 80, 90, 100 or <100% of its 1× concentrations of one or more, or all, of its ingredients, for example, to compensate for effects of incorporating a combustion gas or combustion gas by product. Thus, an AAHKAU or related medium may be used at a relative concentration of 0.1, 0.2, 0.3, 0.4, 0.5, 0.6, 0.7, 0.8, 0.9 or <1× concentration. Preferably, the 1× concentrations of ingredients in AAHKAU medium or similar media are not reduced by more than 1, 2, 3, 4, 5, 6, 7, 8, 9 or 10%.

In other embodiments, AAHKAU medium may have a concentration of one or more, or all, of its ingredients increased above the 1× concentrations disclosed herein, for example, AAHKAU medium may be used at a concentration of 1.1, 1.2, 1.3, 1.4, 1.5, 1.6, 1.7, 1.8, 1.9 or 2.0× to cultivate microalgae. A decreased or increased concentration of AAHKAU medium may be selected to minimize or otherwise compensate for addition of a greenhouse gas or greenhouse gas byproduct. A bioreactor comprising *Haematococcus* sp. KAU-01 or a *Haematococcus* strain that has genomic DNA at least 99% identical to *Haematococcus* sp. KAU-01, an AAHKAU-like medium and one or more ports and/or valves through which fresh medium may be added to a culture and one or more ports and/or valves through which spent medium and/or cellular debris may be removed from a culture without removing viable *Haematococcus* cells.

In some embodiments, the concentration of calcium nitrate $Ca(NO)_3$ in AAHKAU medium prevents cell lysis until the culture pH reaches 9.80. This results in higher biomass production by *Haematococcus* sp. KAU-01 compared to other strains that lyse at a lower pH.

During addition of a gas mixture similar to coal power plant's flue gas, it was found that *Haematococcus* sp. KAU-01 grew in AAHKAU medium over a wide range of pHs from 5.65 to 9.80 without rapturing of cells or forming cysts.

EXAMPLES

The following examples illustrate various aspects of the present invention. They are not to be construed to limit the claims in any manner whatsoever.

Example 1

Isolation of *Haematococcus* sp. KAU-01

Isolation of *Haematococcus* sp. KAU-01. A sample was from Jeddah green valley where the water accumulates from several different mountains using a phytoplankton net with mesh size 10 micron. The sampling location was situated between 21° 36'71"N and 39° 43'16"E to 21° 32'75"N and 39° 28'89"E; see FIGS. 8A-8D. Ten liters of water was filtered using phytoplankton net and concentrated to 500 mL. Water samples were collected from 10 locations. The concentrated sample was mixed with 10 L of NOVA water (Saudi Arabian Nova Water—Health Water Bottling Co. Ltd.) enriched with F/2 medium stock solution (Aquacenter Inc., Leland, Mich., USA; Guillard & Ryther, *Studies of marine planktonic diatoms: I. Cyclotella nana husted, and Detonula confervacea (CLEVE) gran* CANADIAN JOURNAL OF MICROBIOLOGY, 1 Apr. 1962, 8(2); Guillard, *Culture of Phytoplankton for Feeding Marine Invertebrates*, CULTURE OF MARINE INVERTEBRATE ANIMALS, 1975, pp 29-60; each incorporated by reference). One mL of A and B solution was added with 10 liter of NOVA water to grow microalgae which were grown in the transparent NOVA bottles. The culture was grown under 12:12 hrs light:dark (L:D) cycles at 120 µmol photons $m^{-2}s^{-1}$ ($\mu E\ m^{-2}\ s^{-1}$) and at temperature of 25° C. with moderate aeration for 5 days. A one mL sample was taken into S-R chamber from each culture and checked separately under light microscope.

A variety of different microalgae were observed including those of *Haematococcus* sp., *Scenedesmus* sp., *Pediastrum* sp., *Chlamydomonas* sp., *Nostoc* sp, and other diatoms found in wild culture samples. After checking the cultures were kept without aeration for one day to form thin layer scum at the surface water.

When light was provided on the top of culture bottles it was observed that *Haematococcus* formed thin layer scum at the surface of water if the water was not mixed or agitated. A thin layer was observed at the surface of the culture.

Tissue paper was applied to collect the microalgae from the surface. The wet tissue paper was transferred to new culture bottle and the culture was grown as described above. After 5 days, the culture turned green as observed by naked eyes. Then, a 1 mL sample was taken into S-R chamber and microscopically observed. Many motile *Haematococcus* and few *Chlamydomonas* sp., microalgae cells were seen.

A single isolate of *Haematococcus* sp. was recovered using the method described and incorporated by reference to Affan, A., et al., *Growth characteristics, biochemical composition and antioxidant activities of benthic diatom Grammatophora marina from Jeju coast, Korea*. ALGAE, 2006, 21, 141-48. Briefly, 1 mL of the mixed culture sample was diluted with 10 mL distilled water. Then, a 1 mL diluted sample was transferred to a Sedgwick Rafter (S-R) counting chamber, and single cell of *Haematococcus* was picked up with mouth aspirated micropipette (MSM) which was made by heating the tip of a glass Pasteur pipette and then drawing it to form a syringe type needle. The transparent PVC tube was pushed inside of the holder part of glass pasture pipette and finally the joint between glass pasture pipette and PVC tube was made air tight with vacuum latex tube. The length of the PVC tube was kept 75 cm which was convenient and comfortable to hold the tube into mouth and move the glass pasture pipette needle on the S-R chamber or into the multi-well for picking up the single cells. The needle of MSM was placed close to the target a single cell which was observed under an inverted microscope (Olympus IX71) and gently aspirated to isolate the cell inside of the MSM.

Thereafter, each single cell was transferred to a multi-well plate for subculture in culture medium which was prepared in distilled water enriched with F/2 medium and autoclaved. The isolation process was continued until a mono specie was obtained. The mono species was then streaked onto an agar plate with 2% agar (w/v) and two mL/L of "A" and "B" stock solution F/2 and autoclaved distilled water. After two weeks, several green colonies were found in the agar plate.

A single colony from each plated was taken and put in plant tissue multi-culture well plate which was filled with 7.5 mL F/2 enriched distilled water culture medium. Thereafter, each well of multi well was observed under microscope to make sure that the isolated would be single species. The agar plating and liquid culture were continued until obtaining the single species of *Haematococcus* sp. Five mL of an aqueous culture of a single species (or isolate) of *Haematococcus* were poured and mixed in flask which was filled with F/2 enriched agar medium at temperature of 35° C. when the agar was still semi-liquid. This procedure resulted in the isolation of a mono species of *Haematococcus* which was designated *Haematococcus* sp. KAU-01.

Morphological and growth study in different reported media. The isolated microalga *Haematococcus* sp. KAU-01 was examined under a light microscope (LM, Eclipse 80i; Nikon Co.). Images were obtained using a camera (DXM 1200C; Nikon Co.). At first motile cells were observed discover the similarities or differences of their morphological characteristics with reported taxonomical characteristics. Then, life cycle study was conducted and images were taken using same microscope as mentioned above. After that, growth and biomass production study were conducted in various culture media.

$1^{st}$ step of culture in different culture media. The monostrain *Haematococcus* sp. KAU-01, was cultured in BG11 and other media described in Table 1. The chemical composition and concentration of different culture media (1×) used for growing *Haematococcus* sp. KAU-01 is shown in Table 1. It was cultured in BG11 incorporated by reference to Stanier, R. Y., et al., *Purification and properties of unicellular blue-green algae (Order Chroococcales)*; see *Media recipes*, BACTERIOL. REV. 1971, 1971. 35, 171-20; in MBG11 incorporated by reference to Allen, M. M & Stanier, R. Y., *Growth and division of some unicellular blue-green algae*. J. GEN. MICROBIAL. 1968, 51, 199-202; Watanabe, M. M., et al., *NIES-Collection List of* Strains Sixth Edition 2000 *Microalgae and Protozoa*. MICROBIAL CULTURE COLLECTIONS, NATIONAL INSTITUTE FOR ENVIRONMENTAL STUDIES, Tsukuba, 159 pp; in OHM incorporated by reference to Fàbregas, J., et al., *Two-stage cultures for the production of astaxanthin from Haematococcus pluvialis*. JOURNAL OF BIOTECHNOLOGY. 2001, 89: 65-71), in Basal medium incorporated by reference to Hata, N, et al., *Production of astaxanthin by Haematococcus pluvialis in a sequential heterotrophic photoautotrophic culture*. JOURNAL OF APPLIED PHYCOLOGY 2001, 13: 395-402; in RM (Rudic's medium) incorporated by reference to Rudic, V. & Dudnicenco, T., *Process for cultivation of green alga Haematococcus pluvialis (Flotow)*. 2000, MD Patent Nr. a 2000 0154), in HK (Hong-Kong) medium (Kamonpan Kaewpintong, K., et al. *Photoautotrophic high-density cultivation of vegetative cells of Haematococcus pluvialis in airlift bioreactor* BIORESOURCE TECHNOLOGY, 2007, 98: 288-295; and in MCM incorporated by reference to Borowitzka, et al., *Culture of the astaxanthin-producing green alga Haematococcus pluvialis* 1. *Effects of nutrients on growth and cell type*, JOURNAL OF APPLIED PHYCOLOGY, 1991, 3, 295-3074.

TABLE 1

Nutrient composition and concentration (mg/L) of different culture media for *Haematococcus* sp. KAU-01.

| Ingredient | BG11 mg/L | MBG11 mg/L | OHM mg/L | Basal Concentrations mg/L | RM mg/L | HK mg/L | MCM mg/L |
|---|---|---|---|---|---|---|---|
| $HNO_3$ | | | | | | | |
| $NaNO_3$ | 1500 | 1500 | | | 300 | | |
| $KNO_3$ | | | 410 | | | 300 | 200 |
| $K_2HPO_4$ | 40 | 320 | | | 80 | | 20 |
| $KH_2PO_4$ | | | | 150 | 20 | | |
| $Na_2HPO_4$ | | | 30 | | | 30 | |
| $NaH_2PO_4$ | | | | | | 35.5 | |
| $H_3PO_4$ | | | | | | | |
| $Ca(NO_3)_2 \cdot 4H_2O$ | | | | 100 | | | |
| $CaCl_2 \cdot 2H_2O$ | 36 | 36 | 110 | | 58.5 | 73 | 80 |
| $MgSO_4 \cdot 7H_2O$ | 75 | 200 | 246 | 40 | 10 | 24.6 | 100 |
| $Mg(NO_3)_2 \cdot 6H_2O$ | | | | | | | |
| $Na_2CO_3$ | 20 | 100 | | | | | |
| NaCl | | | | | 20 | | |
| Urea | | | | | | | |
| β-$Na_2$glycero phosphate | | | | 50 | | | |
| Citric acid | 6 | 6 | | | | | |
| $(NH_4)_5[Fe(C_6H_4O_7)]_2$ | 6 | 6 | | | | | |
| EDTA—$Na_2$ | 1 | 1 | | 2.71 | | 6.7 | |
| EDTA | | | | | 7.5 | | 0.0198 |
| Vitamin B12 | | | 0.0015 | 0.0001 | | | 0.004 |
| Biotin | | | 0.025 | 0.0001 | | | |
| Thiamine HCl | | | | 0.01 | | | |
| Thiamine | | | | 0.0175 | | | |
| $H_3BO_3$ | 286 | 286 | | | 0.3 | 0.003 | 61 |
| $MnCl_2 \cdot 4H_2O$ | 1.81 | 1.81 | 0.98 | 0.108 | | | 4.1 |
| $MnSO_4 \cdot H_2O$ | | | | | 1.5 | 0.001 | |
| $ZnSO_4 \cdot 7H_2O$ | 0.22 | 0.22 | | 0.066 | 0.1 | 0.014 | 4.1 |
| $Na_2MoO_4 \cdot 2H_2O$ | 0.39 | 0.39 | 12.0 | 0.0075 | | 0.001 | |
| $(NH_4)_6Mo_7O_{24} \cdot 4H_2O$ | | | | | 0.3 | | 38.0 |
| $CuSO_4 \cdot 5H_2O$ | 0.08 | 0.08 | 0.012 | | 0.08 | 0.012 | 6.0 |
| $Co(NO_3)_2 \cdot 6H_2O$ | 0.05 | 0.05 | | | 0.26 | | |
| $FeCl_3 \cdot 6H_2O$ | | | | 5.888 | | | 0.0244 |
| $FeSO_4 \cdot 7H_2O$ | | | | | | 8.3 | |
| $CoCl_2 \cdot 6H_2O$ | | | 0.11 | 0.12 | | 0.0005 | 5.1 |
| Trisaminomethane | | | | 500 | | | |
| Fe(III)citrate$H_2O$ | | | 2.67 | | | | |
| $Cr_2O_3$ | | | 0.075 | | | | |
| $SeO_2$ | | | 0.005 | | | | |

Media were made with the respective amounts of chemical ingredients described above, diluted in distilled water and then autoclaved for 15 mins. A 1.5 liter medium was made for each of culture media recipes. Each culture was grown in one liter Erlenmeyer Flask with 500 mL of each culture medium at temperature of 25° C. under fluorescent lights (120 µE m$^{-2}$ s$^{-1}$) on a 12:12 h L:D photo cycle with moderate aeration for 16 days. All cultures were conducted in triplicate (n=3).

Determination of growth and biomass production. Growth of *Haematococcus* sp. KAU-01 was determined in two ways, one was direct cell counting and another weighing dry biomass. Samples were collected from each flask every other day. For dry biomass estimation, a 20-mL sample was collected from each culture flask, filtered through pre-weighed GF/F Whatman filter paper. A preweighed filter paper that was soaked in distilled water and dried at the same time was used as a blank. The biomass filter paper was kept at 55° C. in an oven, dried and weighed, and the dry weight biomass was calculated as gL$^{-1}$. For cell counting, a 5-mL sample was collected from each culture flask and fixed with 2% of Lugol's iodine solution. The fixed sample was diluted and the cells were counted using a S-R counting chamber under an inverted microscope. Dry biomass and cell counting values were used for plotting as a growth curve.

The specific growth rate (µ), defined as the increase in cell density or dried biomass per unit time was calculated and formulated as follows:

$$\mu = \frac{\ln(X_1/X_0)}{t_1 - t_0}$$

Where $X_0$ and $X_1$ are cell density/dried biomass at the beginning ($t_0$) and end ($t_1$) of a selected time interval between inoculation and maximum cell density dried biomass, respectively. For determining the growth curve of each sample, replicates were counted and the mean value was used.

Preparation of *Haematococcus* sp. KAU-01-culture medium. The condition and biomass production of *Haematococcus* sp. KAU was dependent on the medium they were cultured in. This may be related with different chemicals with different concentrations in above mentioned different cultures media. Some cells lysed during culture in different media and the biomass production was gradually decreasing. Based on these observations, the inventors sought to increase biomass production by providing media and conditions that would keep cells in a motile division state and that would subsequently increase biomass production in a cyst state which is important for industrial scale production of biomass.

The inventors observed that there were more lysed cells in culture media which were prepared without calcium, that cells were weak and plate rather than dark green when a culture medium has a low concentration of magnesium, and that a high concentration of $Ca(NO_3)_2$ arrested culture growth and caused milky turbidity at a pH above 8.50.

Another coincident negative effect microscopically observed in these cultures was that normal, motile swimming mode was disrupted resulting in slow moving or stationary cells when cellular debris aggregated to the flagella and periphery of the transparent cell walls.

Consequently, the inventors developed new culture media that avoided or ameliorated these problems, for example, by gradually adding or titrating Ca and Mg salts such as $Ca(NO_3)_2$ and $Mg(NO_3)_2 \cdot 6H_2O$ to select a concentration of Ca and Mg that did not negatively impact cell growth and biomass production. The concentration of Ca and Mg were 4.83 and 6.46 milligram per liter in the AAHKAU medium formulation showed the best growth of Haematococcus sp., KAU-01. These may be slightly higher when water containing Ca and Mg is used to produce the medium. Preferably, the above concentrations of Ca and Mg do not vary by more than ±1, 2, 3, 4, 5, 10, 15 or 20% in modified forms of AAHKAU medium and preferably, any added Ca and Mg is added as a nitrate salt.

Media stock solutions containing major nutrients such as major nutrients $NaNO_3$, $KNO_3$, $Ca(NO_3)_2$, $Mg(NO_3)_2 \cdot 6H_2O$, $K_2SO_4$, $K_2HPO_4$, $KH_2PO_4$, $MgSO_4 \cdot 7H_2O$, urea, $HNO_3$, and $H_3PO_4$; and as micro nutrients $FeCl_3 \cdot 6H_2O$, $H_3BO_3$, $Co(NO_3)_2 \cdot 6H_2O$, $K_2Cr_2O_7$, $CuSO_4 \cdot 5H_2O$, $MnSO_4H_2O$, $ZnSO_4 \cdot 6H_2O$, $Na_2$-ETDA, and HCl were formulated as disclosed below. For the vitamin solution, thiamine, +D-biotin, and cyanocobalamin were diluted in autoclaved distilled water and during culture 100 μl/L the vitamin stock solution was added in one liter of culture medium.

$2^{nd}$ step of culture to select best culture media. Three stock solutions were prepared, major nutrients ("A"), micronutrients ("B") and vitamins ("C"). Distilled water, filtered natural seawater and autoclaved distilled water was used to make stock solution of "A", "B", and "C", respectively. Then, five concentrations of "A", five concentrations of "B" and a one concentration of "C" stock solutions were added to freshwater to culture of Haematococcus sp KAU.

The chemical concentrations of 1000× stock solution "A" were $NaNO_3$ (375.00 g), $KNO_3$ (75.00), $Ca(NO_3)_2$ (25.00 g), $Mg(NO_3)_2 \cdot 6H_2O$ (55.00 g), $K_2HPO_4$ (45.00 g), $KH_2PO_4$ (40.00 g), $K_2SO_4$ (10.00 g), $MgSO_4 \cdot 7H_2O$ (23.75 g), urea (1.75 g), $HNO_3$ (65.00 ml/L) and $H_3PO_4$ (15 ml/L) which were diluted in autoclaved distilled water and the final volume was made 1 L.

For 10,000× stock solution "B", $FeCl_3 \cdot 6H_2O$ (35.00 g), $H_3BO_3$ (10.00 g), $Co(NO_3)_2 \cdot 6H_2O$ (2.50 g), $K_2Cr_2O_7$ (1.00 g), $CuSO_4 \cdot 5H_2O$ (1.00 g), $MnSO_4H_2O$ (2.50 g) $ZnSO_4 \cdot 6H_2O$ (7.50 g), $(NH_4)_6Mo_7O_{24} \cdot 4H_2O$ (2.50 g), $Na_2$-ETDA (10.00 g) and HCl (10.00 ml) were diluted in filtered natural seawater and finally the volume was made 1 L.

For 10,000× stock solution "C", thiamine (10.00 g), +D-biotin (0.03 g) and cyanocobalamin (0.001 g) were diluted in autoclaved distilled water and finally the volume was made 1 L.

Thereafter, five concentrations of "A", "B" and one concentration of "C" were diluted for making culture medium to test growth of Haematococcus KAU sp.

The diluted concentration of "A" stock solution was 0.5, 0.75, 1.00, 1.25 and 1.50 ml/L to prepare 'A1', 'A2', 'A3', 'A4' and 'A5' culture medium, respectively.

Similarly, the diluted concentration of "B" stock solution was 50.00, 75.00, 100.00, 125.00 and 150.00 μl/L in 'A1', 'A2', 'A3', 'A4' and 'A5' culture medium, respectively.

Stock solution C was added in an amount of 100.00 μl/L to each of 'A1', 'A2', 'A3', 'A4' and 'A5' culture medium, respectively. The chemical concentration given in Table 5, is the final 1× concentration for culture medium and the concentration unit is mg/L for salts and μl/L for acids. In Tables 2, 3 and 5, the concentrations of chemicals are given in mg/L and μl/L.

Tables 2, 3 and 4 show ingredients in each major (A1-A5) and micro stock solution (B1-B5) and square design among major and micronutrients (X1-X5). such as A1, A2, A3, A4 and A5, and five concentrations of micronutrients stock solutions such as B1, B2, B3, B4 and B5, and groups (X1-X5) for square design among major nutrients and micronutrients.

Results of cultivating Haematococcus sp. KAU-01 in the media combinations described by Table 4 are shown by FIGS. 13A-13E. FIG. 13F shows the superior dry biomass produced by culturing Haematococcus sp. KAU-01 in combination A3B3 (AAHKAU) medium in comparison to several conventional culture media.

TABLE 2

Major Nutrients Group

| Chemicals name | A<br>A1<br>mg/L | B<br>A2<br>mg/L | C<br>A3<br>mg/L | D<br>A4<br>mg/L | E<br>A5<br>mg/L |
|---|---|---|---|---|---|
| $NaNO_3$ | 187.50 | 281.25 | 375.00 | 468.75 | 562.5 |
| $KNO_3$ | 37.50 | 56.25 | 75.00 | 93.75 | 112.5 |
| $Ca(NO_3)_2$ | 12.50 | 18.75 | 25.00 | 31.25 | 37.50 |
| $Mg(NO_3)_2 \cdot 6H_2O$ | 27.50 | 41.25 | 55.00 | 68.75 | 82.50 |
| $K_2HPO_4$ | 22.50 | 33.75 | 45.00 | 56.25 | 67.5 |
| $KH_2PO_4$ | 20.00 | 30.00 | 40.00 | 50.00 | 60.00 |
| $K_2SO_4$ | 5.00 | 7.50 | 10.00 | 12.50 | 15.00 |
| $MgSO_4 \cdot 7H_2O$ | 11.88 | 17.81 | 23.75 | 26.69 | 35.63 |
| Urea | 0.88 | 1.31 | 1.75 | 2.19 | 2.63 |
| $HNO_3$ | 32.50 μl | 48.75 μl | 65.00 μl | 81.25 μl | 97.50 μl |
| $H_3PO_4$ | 7.50 μl | 11.25 μl | 15.00 μl | 18.75 μl | 22.50 μl |

TABLE 3

Micronutrients Group

| Chemicals name | B1<br>mg/L | B2<br>mg/L | B3<br>mg/L | B4<br>mg/L | B5<br>mg/L |
|---|---|---|---|---|---|
| $FeCl_3 \cdot 6H_2O$ | 1.75 | 2.63 | 3.50 | 4.38 | 5.25 |
| $H_3BO_3$ | 0.50 | 0.75 | 1.00 | 1.25 | 1.50 |
| $Co(NO_3)_2 \cdot 6H_2O$ | 0.13 | 0.19 | 0.25 | 0.31 | 0.38 |
| $K_2Cr_2O_7$ | 0.05 | 0.08 | 0.10 | 0.13 | 0.15 |
| $CuSO_4 \cdot 5H_2O$ | 0.05 | 0.08 | 0.10 | 0.13 | 0.15 |
| $MnSO_4 \cdot H_2O$ | 0.13 | 0.19 | 0.25 | 0.31 | 0.38 |
| $ZnSO_4 \cdot 6H2O$ | 0.38 | 0.56 | 0.75 | 0.94 | 1.13 |
| $(NH_4)_6Mo_7O_{24} \cdot 4H_2O$ | 0.13 | 0.19 | 0.25 | 0.31 | 0.38 |
| $Na_2$-ETDA | 0.50 | 0.75 | 1.00 | 1.25 | 1.50 |
| HCl | 0.500 μl | 0.750 μl | 0.100 μl | 0.1250 μl | 0.150 μl |

TABLE 4

Design combinations

| X1 | X2 | X3 | X4 | X5 |
|---|---|---|---|---|
| A1 B1 | A2B1 | A3B1 | A4B1 | A5B1 |
| A1 B2 | A2B2 | A3B2 | A4B2 | A5B2 |
| A1 B3 | A2B3 | A3B3 | A4B3 | A5B3 |
| A1 B4 | A2B4 | A3B4 | A4B4 | A5B4 |
| A1 B5 | A2B5 | A3B5 | A4B5 | A5B5 |

An advantageous formulation described by Table 5 ("A3B3" formulation described by the combination of Tables 2 and 3) was designated Affan-Adnan *Haematococcus* King Abdulaziz University or "AAHKAU" culture medium. The concentration of elemental Ca and Mg were 4.33 and 6.46 milligram per liter in the AAHKAU medium formulation. These may be slightly higher when water containing Ca and Mg is used to produce the medium. "Elemental" Ca or Mg refers to the molecular mass of the Ca or Mg component of a compound or salt such as $Ca(NO_3)_2$.

To avoid or minimize turbidity and enhance growth of *Haematococcus* the inventors found that it was important to regulate the concentration of Ca (elemental) and Mg (elemental) from all ingredients in AAHKAU medium or its derivatives between 1, 1.5, 2, 2.5, 3, 3.5, 4, 4.5, 5, 5.5, 6.0, 6.5, 7, 7.5, 8, 8.5, 9, 9.5 and 10 mg/L for elemental Ca and between 1, 1.5, 2, 2.5, 3, 3.5, 4, 4.5, 5, 5.5, 6, 6.5, 7, 7.5, 8, 8.5, 9, 9.5, 10, 10.5, and 11 mg/L for elemental Mg. Preferably the minimum and maximum concentrations of elemental Ca range from 2.41 to 7.24 mg/L (or any intermediate value within this range) and those of elemental Mg range from 3.23 and 9.69 mg/L (or any intermediate value within this range). Typically, the concentration of elemental Ca is regulated to avoid turbidity.

Alternative formulations of AAHKAU medium may be used to culture *Haematococcus* include modified AAHKAU medium produced by other combinations of A1-A5×B1-B5 (see Table 4, for example) or produced by varying the concentration of one or more ingredients in formulations A3 or B3 by 1, 2, 3, 4, 5, 6, 7, 8, 9, 10, 15, 20, 25, 30, 35, 40, 45 or 50%. Affan-Adnan-*Haematococcus*-King Abdulaziz University (AAHKAU).

TABLE 5(A)

Chemical composition and 1X (mg/L and µml/L) concentrations of *Haematococcus* sp KAU culture medium AAHKAU for the obtaining rapid growth and biomass production.

| 1X AAHKAU Medium | | | | | |
|---|---|---|---|---|---|
| A-solution Chemicals | Conc. mg/L | B-Solution Chemicals | Conc. mg/L | C-Solution Chemicals | Vitamins mg/L |
| $NaNO_3$ | 375.00 | $FeCl_3 \cdot 6H_2O$ | 3.50 | Thiamine | 1.00 |
| $Ca(NO_3)_2$ | 25.00 | $H_3BO_3$ | 1.00 | +D-biotin | 0.003 |
| $Mg(NO_3)_2 \cdot 6H_2O$ | 55.00 | $Co(NO_3)_2 \cdot 6H_2O$ | 0.25 | Cyanocobalamin | 0.0001 |
| $K_2HPO_4$ | 45.00 | $K_2Cr_2O_7$ | 0.10 | | |
| $KH_2PO_4$ | 40.00 | $CuSO_4 \cdot 5H_2O$ | 0.10 | | |
| $KNO_3$ | 75.00 | $MnSO_4 \cdot H_2O$ | 0.25 | | |
| $K_2SO_4$ | 10.00 | $ZnSO_4 \cdot 6H2O$, | 0.75 | | |
| $MgSO_4 \cdot 7H_2O$ | 23.75 | $(NH_4)_6Mo_7O_{24} \cdot 4H_2O$ | 0.25 | | |
| Urea | 1.75 | $Na_2$-ETDA | 1.00 | | |
| $HNO_3$ | 65.00 µl | HCl | 1.00 µl | | |
| $H_3PO_4$ | 15.00 µl | | | | |

The pH is typically adjusted to 7.5 by adding $Na_2CO_3$.

TABLE 5(B)

The chemicals name and concentrations for a 1000X stock solution (g/L or ml/L) of A-solution and 10000X stocks of B- and C-solutions for AAHKAU medium for *Haematococcus* sp., KAU-01.

| Stock Solutions | | | | | |
|---|---|---|---|---|---|
| A-solution (1000x) Chemicals | Conc. g/L | B-Solution (10,000X) Chemicals | Conc. g/L | C-Solution (10,000X) Chemicals | Vitamins g/L |
| $NaNO_3$ | 375.00 | $FeCl_3 \cdot 6H_2O$ | 35.00 | Thiamine | 10.00 |
| $Ca(NO_3)_2$ | 25.00 | $H_3BO_3$ | 10.00 | +D-biotin | 0.03 |
| $Mg(NO_3)_2 \cdot 6H_2O$ | 55.00 | $Co(NO_3)_2 \cdot 6H_2O$ | 2.50 | Cyanocobalamin | 0.001 |
| $K_2HPO_4$ | 45.00 | $K_2Cr_2O_7$ | 1.00 | | |
| $KH_2PO_4$ | 40.00 | $CuSO_4 \cdot 5H_2O$ | 1.00 | | |
| $KNO_3$ | 75.00 | $MnSO_4 \cdot H_2O$ | 2.50 | | |
| $K_2SO_4$ | 10.00 | $ZnSO_4 \cdot 6H2O$, | 7.50 | | |
| $MgSO_4 \cdot 7H_2O$ | 23.75 | $(NH_4)_6Mo_7O_{24} \cdot 4H_2O$ | 2.50 | | |
| Urea | 1.75 | $Na_2$-ETDA | 10.00 | | |
| $HNO_3$ | 65 ml | HCl | 10.00 ml/L | | |
| $H_3PO_4$ | 15 ml/L | | | | |

This advantageous formulation was designated Affan-Adnan *Haematococcus* King Abdulaziz University or "AAHKAU" culture medium. In some embodiments, an AAHKAU-like medium may be produced by varying the concentrations of one or more of the above-named ingredients by 1, 2, 3, 4, 5, 6, 7, 8, 9, 10, 15, 20, 25, 30, 35, 40, 45 or 50%. More concentrated stock solutions of the A-, B- and C-solutions in Table 5 may be formulated by increasing the amounts of chemical ingredients with respect to water content. For example, a 1000× concentrated solution may be produced by replacing the units in Table 5 "mg/L" for salts and vitamins with g/L and replacing "μl/L" for acids with "mL/L". A 1× solution can then be produced by diluting 1 ml of 1000× concentrated stock solution-A and 0.1 ml of each of 10,000× stock solutions B and C up to 1 L with water thus producing a 1× medium for growing *Haematococcus* sp. KAU-01.

$3^{rd}$ step of culture. After formulation of the medium, *Haematococcus* sp. KAU-01 was grown in AAHKAU medium and other reported media (OHM, RM, Basal and HK media) to compare the growth performance. For growth study in AAHKAU medium, two types of water were used, one was distilled water which was name as AAHKAU-land another was tap water from the municipal water supply which was named as AAHKAU-2. Both of AAHKAU-1 and AAHKAU-2 were kept 4 hours after adding of stock solutions of AAHKAU culture medium at low pH (2.88), since stock solution-A and B were highly acidic (pH≅0.18). The pH was then adjusted to 7.00 by adding $Na_2CO_3$. The culture was done in two liter Erlenmeyer flasks containing 1000 mL of each culture medium. The culture comparisons were conducted at same light intensity and temperature with L:D cycle of 12:12 hr. Gentle aeration was provided continuously provided to agitate the culture.

Microscopic observations. Morphological characteristics of the isolated microalga were investigated under inverted light microscope (LM) and photographed. LM based analysis was done from the mono species isolated *Haematococcus* sp. KAU-01 microalga.

Vegetative motile cell with two flagella, semitransparent trilaminar sheath between cytoplasm, cytoplasmic strands that attaches the main cell body to the theca or the outer cell wall and pyrenoids were observed under inverted light microscope (FIG. 9). The shapes of biflagellate vegetative cells were ovoid to ellipsoidal averaging 27.7±3.3 μm in length and 22.0±4.2 μm in diameter (FIG. 10A).

During the laboratory culture, the flagellated cells were changed to immotile intermediate cells which were palmelloid with some astaxanthin accumulation; see FIGS. 10A and 10B. Within 2-3 days the cells turned into red cysts cells or aplanospores; FIG. 10C. An average diameter of both immotile with central red and green toward periphery or red spherical palmelloid cells were 35.6±8.2 μm. The average diameter of the relatively large red cyst cells diameter was above 65 μm; FIGS. 10B and 10C.

The red cyst started asexual reproduction after 2 days of inoculation into new culture medium (FIG. 10D and FIG. 10E) then the daughter cells came out by breaking cell wall (FIG. 10F). Cells of the palmelloid stage reproduced asexually by cell division and formed 4 to 64 zoospores (FIG. 10D and FIG. 10E).

In other culture media, lysed cells were seen and sometimes whole cultured cells or some of culture was found to be lysed without forming cyst. Lysis could be stopped by gradually increasing the concentration of $Ca(NO_3)_2$ up to 25.00 mg/L (1.83 mg/L elemental Ca) which is the amount in 1× AAHKAU medium as this concentration was considered as the primary concentration for making the AAHKAU *Haematococcus* sp. KAU-01 culture medium. The fate of cells cultured without addition of $Ca(NO_3)_2$ is shown in FIGS. 11A-11D.

In some embodiments or variations of this novel medium, an elemental calcium concentration may be selected as an amount sufficient to prevent or sufficient reduce lysis to 0, 5, 10, 20, 30, 40, 50, 60, 70, 80 or 90% of a control lysis value of a culture having no or less than 1, 2, 3, 4, 5, or 6 mg/L elemental calcium. Preferably the content range of elemental Ca is 2.41 to 7.24 and the content range of elemental Mg is 3.23 to 9.69 mg/L in AAHKAU medium or a variation thereof.

Figure 12A:
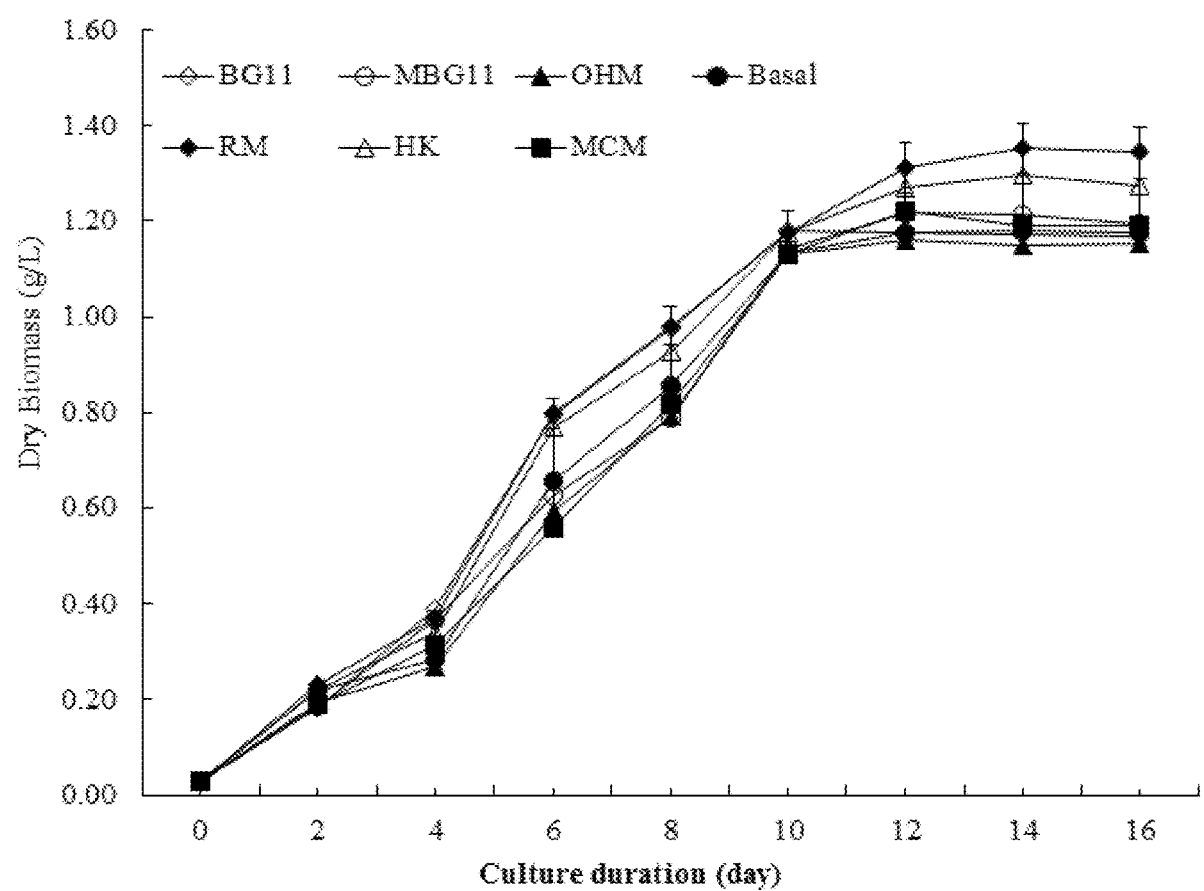
FIG. 12A. Growth performance and biomass (dry wt. $gL^{-1}$) production of *Haematococcus* sp. KAU-01 grown in seven different culture media as comparable to AAHKAU medium.

Growth and biomass production in different culture media in $1^{st}$ step of culture. The dry biomass production ($gL^{-1}$) differed depending on the selected culture media. Moreover, peak growth in view of biomass production occurred at different times or different days depending on the culture medium selection. In BG11 culture medium, the highest biomass production was 1.18 $gL^{-1}$ on $10^{th}$ day of culture. Similarly, in MCM, MBG11 or OHM culture medium the highest biomass production, respectively, 1.22, 1.22 and 1.16 $gL^{-1}$ on $12^{th}$ day of culture. Biomass production in Basal, HK and RM culture media were 1.18, 1.29 and 1.35 $gL^{-1}$ on $14^{th}$ day of culture (FIG. 12A). However, the highest biomass production was in RM culture medium, followed by HK and Basal media (FIG. 12A).

Figure 12B:
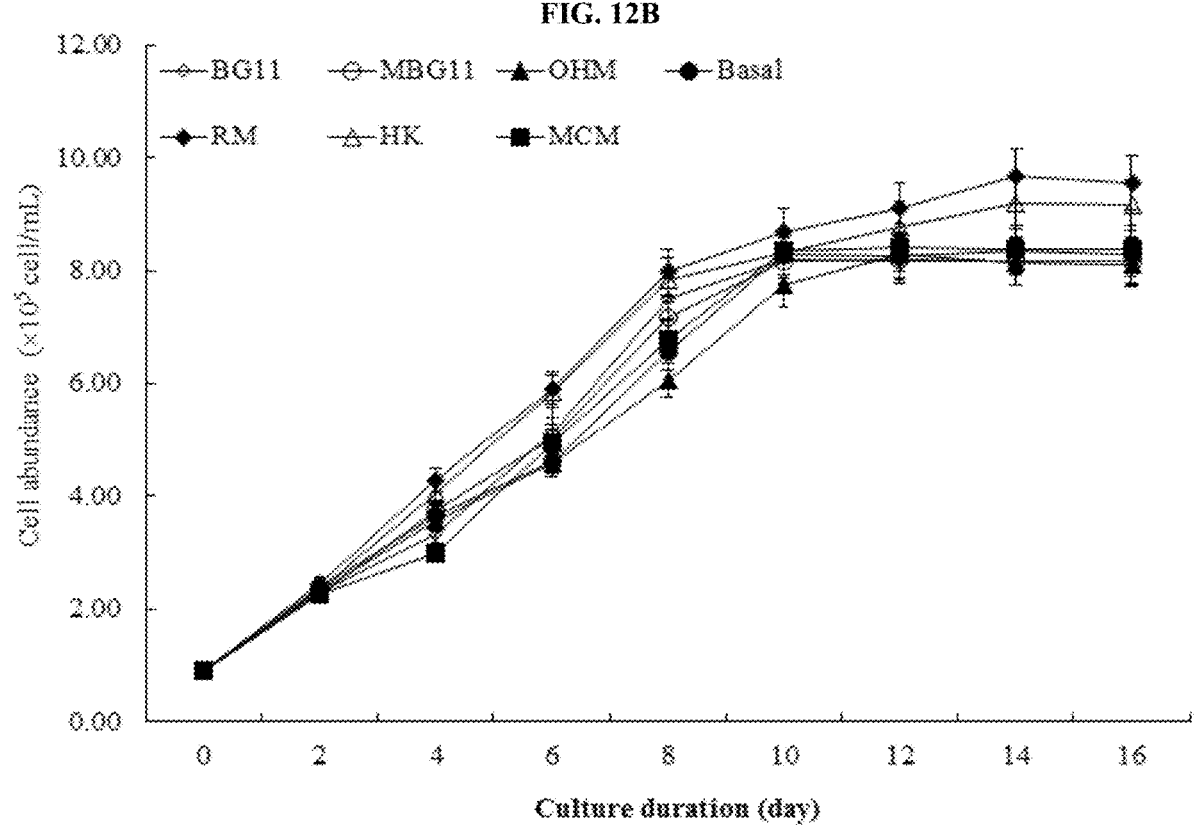
FIG. 12B. Growth performance and cell abundance of *Haematococcus* sp. KAU-01 grown in seven different culture media as comparable to AAHKAU medium.

The result of cell abundance *Haematococcus* sp. KAU-01 also showed similar growth pattern as it was found in dry biomass estimation. In BG11 culture medium the highest cell abundance was 8.19×10^5 cells $L^{-1}$ on $10^{th}$ day of culture. Similarly, in MBG11, OHM and MCM culture media, the maximum cell abundance respectively was 8.19×10^5, 8.27×10^5 and 8.40×10^5 cells $L^{-1}$ on $12^{th}$ day of culture. However, the highest cell abundance among the culture was 9.67×10^5 cells $L^{-1}$ in RM culture medium, followed by HK (9.20×10^5) and basal (8.34×10^5) culture media on $14^{th}$ day of culture (FIG. 12B).

Growth of *Haematococcus* sp. KAU-01 in AAHKAU culture medium in the $2^{nd}$ step of culture. *Haematococcus* sp. KAU grew well in all square combinations of A and B stock solutions mixed culture media. The higher biomass production was in major nutrient C group (media combinations A3B1; A3B2; A3B3; A3B4; A3B5) than those of A, B, D and E groups. In C group, the biomass production was 1.86 $gL^{-1}$ in A3B3, followed by A3B4 and A3B5 (FIGS. 13A, 13B, 13C, 13D and 13E). Therefore, AAHKAU (A3B3) culture medium recipe was considered to be the most advantageous medium for growth of *Haematococcus* sp. KAU-01 and designated AAHKAU medium.

Figure 14A:
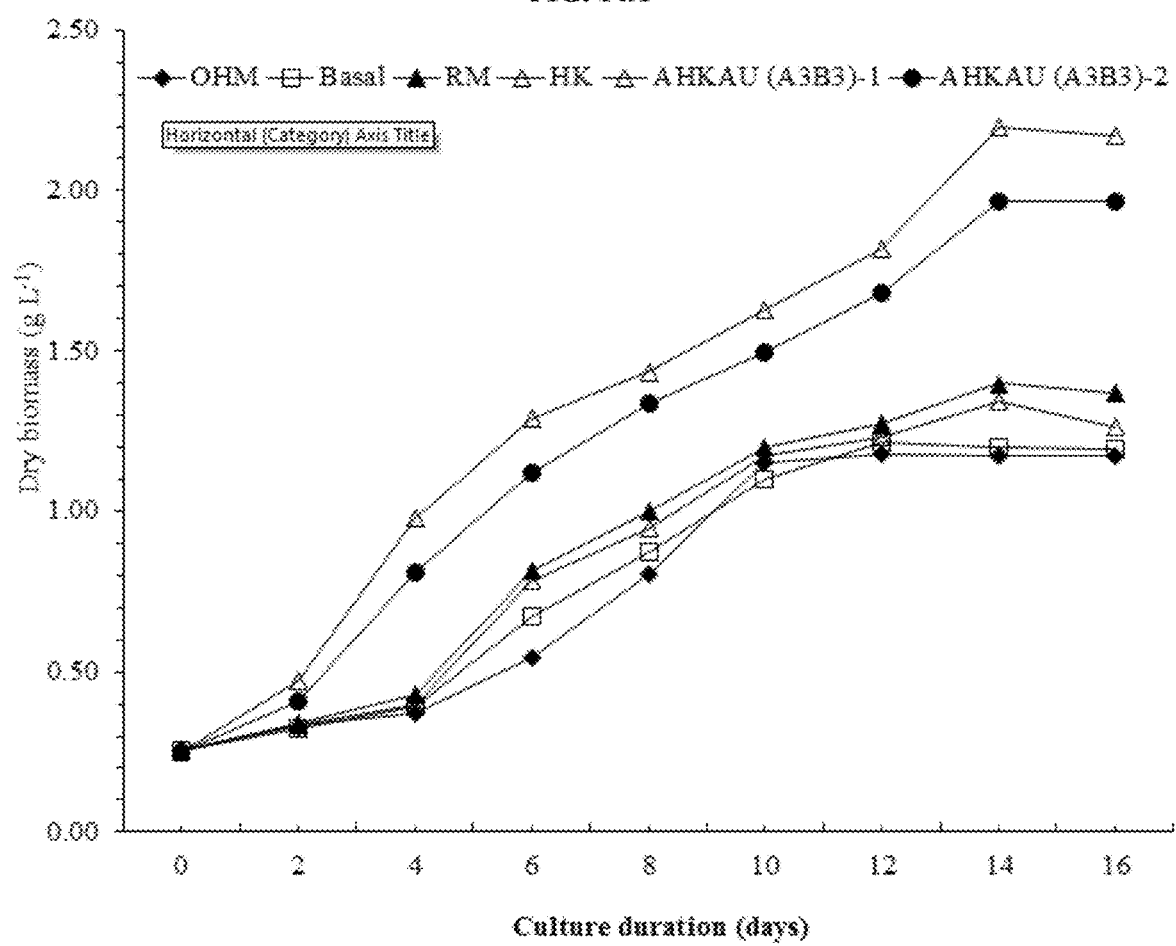
FIG. 14A. Variation of biomass production of *Haematococcus* sp. KAU-01 grown in comparative culture media OHM, Basal, RM, HK and AAHKAU (A3B3) 1 (sterile filtered, distilled water) and AAHKAU (A3B3) 2 (non-sterile tap water). AAHKAU-1 was prepared autoclaved sterile distilled water and AAHKAU-2 was prepared using municipal supplied water which has been not been directly acid treated, but which was made acidic after dilution of stock solution of 'A' and 'B' as both solution contain acids.

For the final step of culture in selected AAHKAU and reported media a *Haematococcus* sp. KAU-01 growth experiment was conducted to compare the growth and biomass production with other conventional media. *Haematococcus* sp. KAU-01 was grown in OHM, Basal, RM, HK and AAHKAU (A3B3) culture media. The biomass production was highest 2.20 $gL^{-1}$ in AAHKAU medium, followed by RM (1.37 $gL^{-1}$) and HK (1.31 $gL^{-1}$), respectively (FIG. 14A). Maximum specific growth ($\mu_{max}$ $d^{-1}$) rate was 0.161 and 0.163 $d^{-1}$ on $12^{th}$ day of culture in basal and OHM culture media.

Figure 14B:
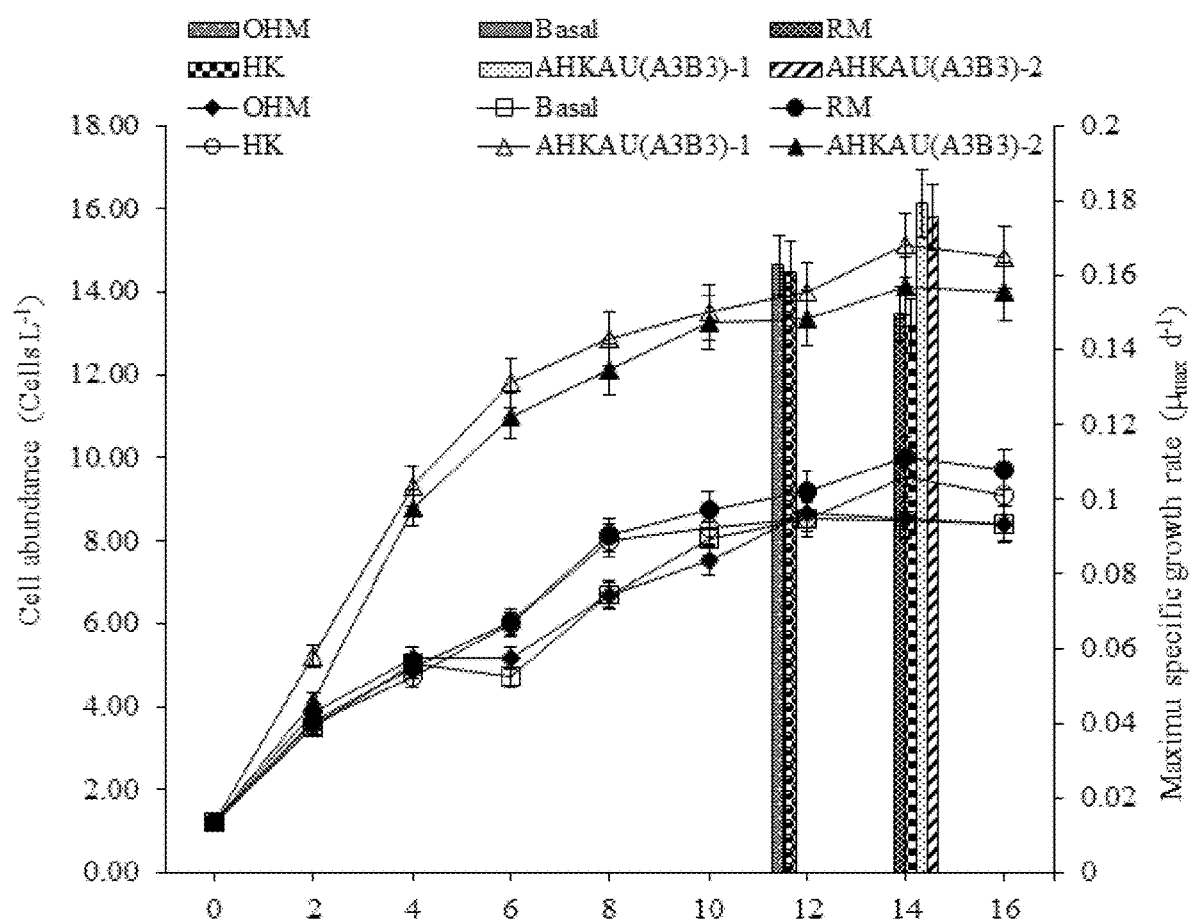
FIG. 14B. Variation in maximum specific growth rate (umax $d^{-1}$) and growth curve with cell abundance (Cells $L^{-1}$) of *Haematococcus* sp. KAU-01 cultured in different culture media including newly prepared AAHKAU (A3B3) medium.

The highest the $\mu_{max}$ $d^{-1}$ was 0.179 $d^{-1}$ on $14^{th}$ day of culture in AAHKAU-1, followed by 0.150 and 0.146 $d^{-1}$ in RM and HK media, respectively on same day of culture. In case of AAHKAU-2, the biomass production, cell abundance and $\mu_{max}$ $d^{-1}$ were 1.96 $gL^{-1}$, 14.13×10^5 cells $L^{-1}$ and 0.174 $d^{-1}$, respectively (FIG. 14B).

Morphological features of *Haematococcus* sp. KAU-01 are illustrated in FIG. 9. The motile cell having several pyrenoids, two flagella and cytoplasmic strands connecting with main cell body and outer cell wall were observed under inverted light microscope. The motile flagellated cell typically exhibits a voluminous, transparent and gelatinous looking cell wall which is the characteristic of Volvocalean motile cells. *Haematococcus* sp. are characterized by ovoid, ellipsoid or spherical cells and 34-37.5 µm in diameter (up to 5 µm broad and 63 µm long). The cell wall is widely separated from the protoplast without a papilla, protoplast with a beak-like apex not reaching up to the wall, plasma strands branched and connected with cell wall, chloroplast with thick membrane having 6-8 (up to 15) scattered pyrenoids. These microscopic characteristics are similar to motile cells of *Haematococcus* sp. KAU-01.

During the laboratory culture, the flagellated cells converted to immotile intermediate cells (palmelloid with some astaxanthin accumulation). Those cells were picked up following MSM technique and kept into multiwall tissue culture plate with distilled water under same light condition as culture. After 3 days all intermediate cells turn into deep red cyst. The red cysts again inoculated into fresh media and observed after certain interval for changing to different stage of life cycle. There were 4 to 64 daughter cells were observed in the red cyst and after few hours the daughter cells ruptured the cell wall of the cyst and motile cells came out and start to multiply. A similar observation was made by Hagen et al. (2001) who indicated that the developmental cycle of *Haematococcus pluvialis*, flagellates are formed by germination of resting cells after getting favorable environmental condition. Consequently, the inventors place their isolate within the genus *Haematococcus* sp. based on light microscopic study of motile cells and life cycle of this alga. This new isolate and species within this genus was designated *Haematococcus* sp. KAU-01.

During culture of *Haematococcus* sp. KAU-01, the broken or lysed cells were observed in the culture medium prepared without or with low concentrations of calcium salts. The cell wall of *Haematococcus* sp. KAU-01 was not broken or ruptured when $Ca(NO)_3$ concentrations ranged from 12.50 to 37.50 $mgL^{-1}$ in culture medium where 25.00 $mgL^{-1}$ of $Ca(NO)_3$ gave the best result for growth. A higher concentration was found to stop the movement of flagellated motile cells and inducing to form cyst. The inventors observed that *Haematococcus* sp. KAU-01 grew between pH 5.65 and 9.80 without significant lysis or rupture of cells or formation of cysts. They also found that a suitable concentration of calcium protected *Haematococcus* from lysis at least until the pH of the culture medium exceeds 9.8. This inhibition of cell lysis enhanced biomass yield. Additionally, calcium nitrate salts were used rather than calcium chloride or calcium phosphate. During photosynthesis chloride ions play a role in balancing of potassium and in water splitting however, nitrate plays an important role as a major plant nutrient. Calcium phosphate makes the culture medium milky turbid when adjusted to pH 7.5. The nitrate supplied by calcium nitrate also plays a role in biosynthesis of amino acids and for total protein and carbohydrate production of cells.

Growth and biomass production in different culture media. The growth rate and biomass production of *Haematococcus* sp were influenced by several physical and chemical factors. Chemical factors include selection of proper combinations of macro and micronutrients and physical factors include culture temperature and illumination. The inventors found that *Haematococcus* sp. KAU-01 showed similar growth as *H. pluvialis* when *Haematococcus* sp. KAU-01 was cultured under at light intensity of 120 $\mu E\ m^{-2}\ s^{-1}$ on a 12:12 L:D photo cycle. However, surprising results were obtained when *Haematococcus* sp. KAU-01 was grown in AAHKAU medium and other reported media at 100 $\mu E\ m^2\ s^{-1}$ on a 12:12 h L:D photo cycle. The cell abundance and biomass production were higher in light intensity of 100 $\mu E\ m^{-2}\ s^{-1}$ than that of 120 $\mu E\ m^{-2}\ s^{-1}$ under same L:D photo cycle intensity in all culture media.

Among the all culture, the highest cell abundance, $\mu maxd^{-1}$ and biomass production were in AAHKAU culture medium. RM, BG11 and Basal media are more often used for growing *H. pluvialis*. Among those media, RM and basal media showed the higher cell abundance which was $9.50 \times 10^5$ and $8.85 \times 10^5$ cells mL–1, and the maximum specific growth rate was 0.195 and 0.177 d–1, respectively. The remarkable growth, cell abundance and biomass production achieved in AAHKAU medium exceeded that of any other reported culture media. While not being bound to any theory or explanation, the inventors believe that the $Ca^{2+}$, $Mg^{2+}$, and $NO_{3-}$ content of AAHKAU medium in combination with large amount of iron may protect against cell wall lysis, increase chlorophyll content and protein synthesis and ultimately enhance growth and biomass production.

To test the effects of culturing *Haematococcus* in tap water a comparative AAHKAU-2 culture was performed using tap water to observe the growth and biomass production by eradication of contaminant species by adding of acidic stock solution of AAHKAU. In AAHKAU-2 culture, *Haematococcus* sp. KAU-01 grew well in comparison with reported media and there were no more contaminant species found. In tap water some microalgae (*Scenedesmus* sp. *Chlamydomonas* sp., etc.) was found to grow after enriched with F/2 culture medium nutrients during trial error study of growth of *Haematococcus* sp. KAU-01. It was also observed that growth of *Haematococcus* sp. KAU was stopped in presence of contaminating microalgae, for example, *Haematococcus* sp. KAU-01 was lost from a culture containing *Scenedesmus* sp. KAU-01. Biomass production was lower in AAHKAU-2 (tap water) than that the biomass production of AAHKAU-1.

In Jeddah, tap water for domestic use is supplied from desalination plants for domestic use. The desalinated water contains 100-1000 $mgL^{-1}$ of total dissolved solids, and the concentration of calcium is almost 200 $mgL^{-1}$ of water; Hussein, M. & Magram, S. F., *Domestic Water Quality in Jeddah, Saudi Arabia*. JKAU: ENG. SCI. 2012, 23, 207-223. High concentrations of $Ca^{2+}$ might have played role to slow growth of *Haematococcus* sp. KAU-01 as discussed above.

This Example shows for the first time the morphological characteristics and preparation of optimum culture medium for isolated *Haematococcus* sp. KAU-01 in KSA and the GCC. The new strain grew in all the reported culture media. Additionally, it showed massive growth in newly optimized culture medium (AAHKAU) in batch culture. Ca salt concentration in AAHKAU medium was confirmed to prevent or resist cell wall lysis. AAHKAU medium stock solutions also conferred the ability to eradicate microbial contaminants found in water that is not autoclaved such as tap water. Consequently, autoclaving of water or culture medium is not needed before inoculation of *Haematococcus* sp. for their culture and this provides a way to perform large scale outdoor culture for industrial scale biomass using AAHKAU culture medium, particularly in hot tropical countries like the Kingdom of Saudi Arabia and GCC countries using *Haematococcus* sp. KAU-01 which was locally isolated from a hot tropical climate.

Example 2

Culture of *Haematococcus* sp. KAU-01 with Normal Aeration and/or in Presence of Combustion Gases As shown herein the inventors have developed a culture medium and methods useful for convenient and economical large scale biomass production from microalgae that mitigates or eliminates atmospheric pollution caused by flue gases emissions from fossil fuel power plants while enhancing microalgae growth and biomass production.

Materials and methods. Three stock solutions, "A" for major nutrients, "B" for micronutrients and "C" for vitamins were prepared as described above. To produce a 1× AAHKAU culture medium as described in Table 5 approximately 1.0, 1.0 and 1.0 ml of stock solution of 'A', 'B' and 'C' were respectively diluted into 1 L of water. Two types of water used to prepare the culture medium, one was distilled water and another one was municipal water. After dilution of stock solutions, the water pH was checked which was about 3.0 and $Na_2CO_3$ was added to adjust the pH to pH 7.00 prior to inoculating the 1× medium with *Haematococcus* sp. KAU-01 for growth and biomass production. The study was carried out until all the motile cells turn to inactive cysts.

Three groups of culture experiments A, B and C were designed to identify the best culture conditions for with *Haematococcus* sp. KAU-01.

The cultures in Group A (A1, A2 and A3) were continuously aerated with normal air to agitate the cultures, those in Group B (B1, B2 and B3) were given 15% $CO_2$ gas periodically after day 4 of culture along with continuous normal aeration, and those in Group C (C1, C2 and C3) were given mixture gases (15% $CO_2$+5% CO+1% NO+1% $NO_2$) periodically after the fourth day of culture along with continuous normal aeration.

The A1 culture was done with adding of initial concentrations of stock solutions of AAHKAU medium (solution A, B and C of AAHKAU medium at 3.5, 1.0 and 1.0 ml/L) to produce 1× medium.

Initial nutrients concentration of A2 medium was same as regards to the initial nutrients concentration of A1, and after four days of culture a continuous nutrients of AAHKAU medium was provided to the A2 culture. For that, initial concentrations of stock solutions of AAHAKU medium was diluted 2.5 times in distilled water. Thereafter, the diluted stock solutions were added continuously to maintain constant pH of 7.5, since stock solution of AAHAKU medium is highly acidic. The diluted AAHKAU medium was added with a pH controller and dosing pump (BL7916-2 pH Controller with Pump, Hanna, Instrument Co.)

The A3 culture was same as regards to A1 culture except exchange of 20% ongoing culture medium with fresh initial concentration of AAHKAU medium concentration after four days of culture. The exchange of culture medium was done on every third day.

In B1 culture, $CO_2$ gas was provided periodically after four days of culture to adjust the pH 7.5. $CO_2$ gas was provided to the culture during the light period to adjust pH of 7.5. The culture pH was checked hourly and $CO_2$ gas was provided to the culture.

The B2 culture was the same as the B1 culture except for addition of 2.5 times dilute, initial concentration of AAHKAU medium stock solutions to adjust pH of 7.5 once in a day after four days of culture while rest of the time the pH was adjusted 7.5 with periodically providing of $CO_2$ gas to the culture. $CO_2$ gas was provided following the same way as described in B1 culture.

The B3 culture was same as regards to B1 culture except exchange of 20% ongoing culture medium with fresh initial concentration of AAHKAU medium. The exchange of 20% ongoing culture medium of B3 was same as regards to A3 culture. And $CO_2$ gas was provided as described for the B1 culture.

In the C1 culture, the mixture gages ($CO_2$ 15%+CO 5%+NO 1%+$NO_2$ 1%+$N_2$ balance) was provided periodically after four days of culture to adjust the pH of 7.5. The mixture gases were provided following the same way as described for the B1 culture.

The C2 culture was same as the C1 culture except for addition of 2.5 times diluted stock solution of AAHKAU medium once in a day to adjust pH 7.5 after four days while the rest of the time pH was adjusted 7.5 with mixture gases. Periodically providing of mixture gases was same as described for the C1 culture.

The C3 culture was same as regards to C1 except exchange of 20% ongoing culture medium with fresh initial concentration of AAHKAU medium. The exchange of 20% medium was same as regards to A3 culture. Periodical providing of mixture gases was same as described for the C1 culture.

Exchange of culture medium in A3, B3 and C3 was done by discharging of 20% old culture medium through filtration and replacement of newly prepared culture medium (initial concentrations of nutrients). For exchanging, a 5.00 micronmesh size filter bag (Zhengzhou Mining Machinery, Co. Ltd, China) was cut and sacks were made. Sacks were 15 cm long and 10 cm wide with a small opening where one side of clear flexible 4 mm air tube of 1.5 meter length was pushed inside of sacks and fixed with Gorilla super glue and cellophane. Then, one side of vein saline tube was pushed inside of the flexible tube and fixed tightly with cellophane and another part a regulator was kept to control the out flow of culture medium. Thereafter, the culture medium was allowed to discharge by gravitation force and flow speed was controlled by the regulator. The alga that attached to the sack's surface was removed by reverse forced air flow.

Culture medium exchange was stopped when 90% motile cells turned into cysts. The culture was grown in transparent 12 L NOVA bottles (Health Water Bottling Company, the Kingdom of Saudi Arabia, hypertext transfer protocol:// worldwideweb.novawater.com/en/index.php).

The upper parts of the bottles were cut to form a cylindrical photobioreactor. Each bottle was filled up with 10 liters AAHKAU culture medium. The culture was grown at temperature of 25° C. under fluorescent lights (1804 $m^{-2}$ $s^{-1}$) on a 14:10 h L:D light dark photo cycle for 26 days. All cultures were conducted in triplicate (n=3).

Determination of growth and biomass production. The growth of *Haematococcus* sp. KAU-01 was determined in two ways. One was direct cell counting and the other weighing dry biomass. Samples were collected from each flask every other day.

For dry biomass estimation, a 20 mL sample was collected from each culture flask, filtered through preweighed GF/F Whatman filter paper. A preweighed filter paper that was soaked in distilled water and dried at the same time was used as a blank. The biomass filter paper was kept at 55° C. in an oven, dried and weighed, and the dry weight biomass was calculated as g/L.

For determination of particulate materials, 250 mL discharge water was filtered and dried using filter paper following the same procedure used for biomass determination and expressed as mg/L.

For cell counting, a 5 mL sample was collected from each culture flask and fixed with 2% of Lugol's iodine solution. The fixed sample was dilute and the cells were counted using a S-R counting chamber under an inverted microscope.

A growth curve was plotted using the dry biomass and cell counting values. The specific growth rate (μ), defined as the increase in cell density or dried biomass per unit time (Pirt 1975), was calculated and formulated as follows:

$$\mu = \mathrm{Ln}(X1/X0)/(t1-t2) \qquad (i)$$

where $X_0$ and $X_1$ are cell density/dried biomass at the beginning ($t_0$) and end ($t_1$) of a selected time interval between inoculation and maximum cell density dried biomass, respectively. For the growth curve of each sample, replicates were counted and the mean value used.

Microscopic study was done to evaluate the formation of palmella from vegetative cells (two equal flagella). The density of palmella was found to be 90% on the next sampling day of maximum specific growth in each culture.

In the A culture group, more than 90% of palmella were found to be formed on days 16, 18 and 20 of culture in A1, A2, and A3 culture, respectively.

In the B culture group, a similar amount of percentage of palmella found on 20, 22 and 24$^{th}$ day of culture in 'B1, B2, and B3, respectively.

Figure 2:
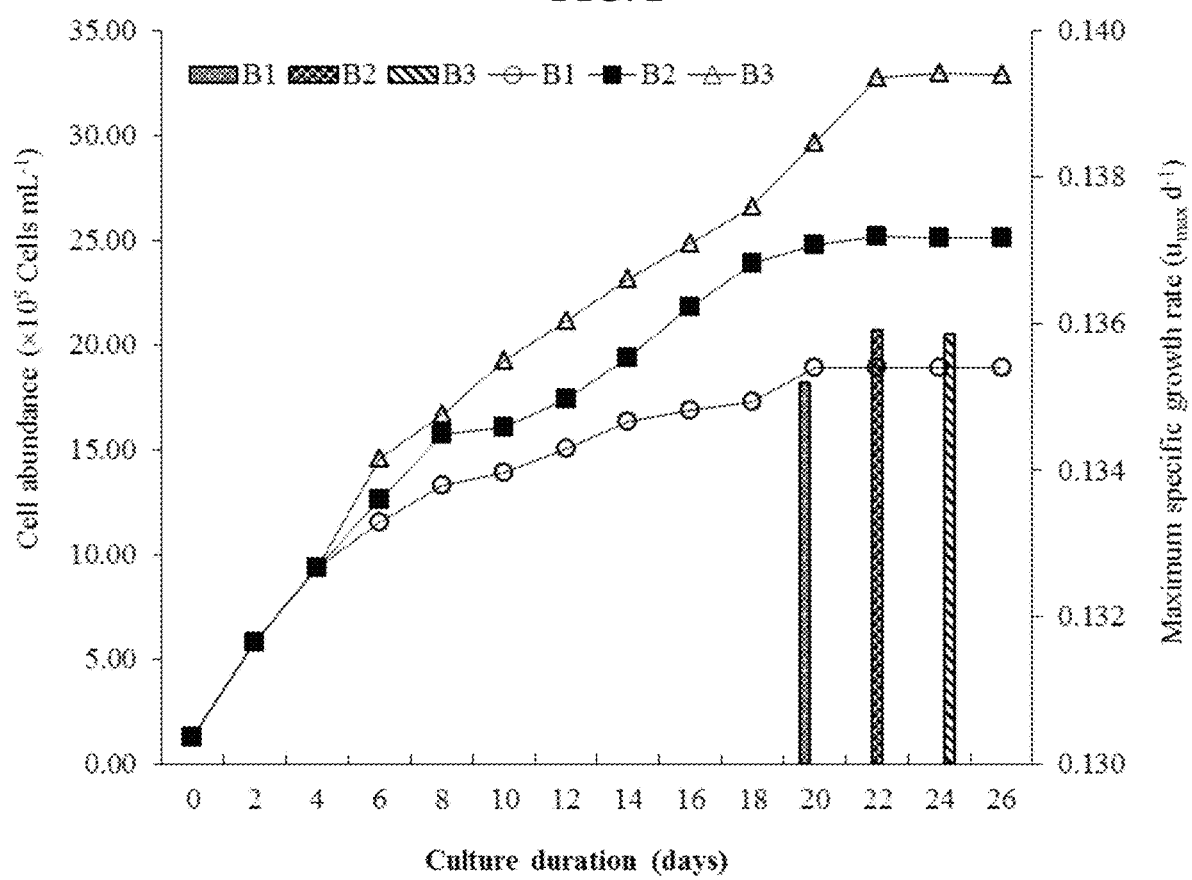
FIG. 2. Variation in maximum specific growth rate ($u_{max}$ $d^{-1}$) and growth curve with cell abundance (×$10^5$ cells $mL^{-1}$) of *Haematococcus* sp. KAU cultured in AAHKAU medium within 'B' culture group. B1 normal aeration+15% $CO_2$; B2: normal aeration+15% $CO_2$, pH maintained at pH 7.5 and additionally pH was maintained 7.5 by injecting of stock solution A and B on alternative day; B3: normal aeration+15% $CO_2$, 20% media replacement on alternate days.
Figure 3:
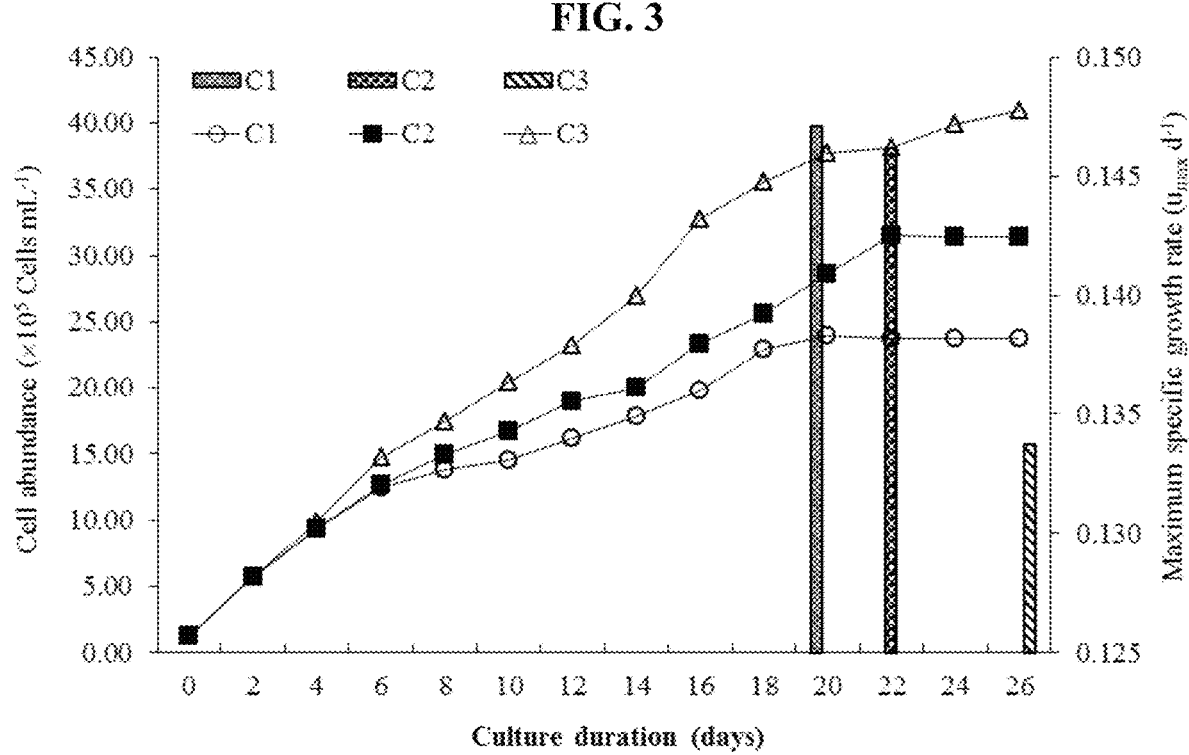
FIG. 3. Variation in maximum specific growth rate ($u_{max}$ $d^{-1}$) and growth curve with cell abundance (×$10^5$ cells $mL^{-1}$) of *Haematococcus* sp. KAU cultured in AAAHKAU medium within "C" culture group: C1 normal aeration+15% $CO_2$+CO 5%+NO 1%+$NO_2$ 1%+$N_2$ balance; C2: normal aeration+15% $CO_2$+CO 5%+NO 1%+$NO_2$ 1%+$N_2$ balance, pH maintained at pH 7.5, and additionally pH was maintained 7.5 by injecting of stock solutions A and B on alternate days; C3: normal aeration+15% $CO_2$+CO 5%+NO 1%+$NO_2$ 1%+$N_2$ balance, 20% media replacement on alternate days.

Similarly, in the C culture group, it was observed on 20, 24 and 26$^{th}$ day of culture in C1, C2 and C3, respectively (FIGS. 1, 2 and 3).

Cell abundance and Biomass production. Maximum specific growth rate ($\mu_{max}$ d$^{-1}$) is an informative way to ascertain microbial activity which can increase at exponential rates. Growth characteristics determination under controlled conditions can play significant biological information for mass culture of *Haematococcus* sp.

The $\mu_{max}$ d$^{-1}$ of *Haematococcus* sp. KAU-01 varied from 0.138 to 0.157 (see bars in FIG. 1), 0.135 to 0.136 (see bars in FIG. 2) and 0.134 to 0.147 d$^{-1}$ (see bars in FIG. 3) in culture groups 'A', and 'C', respectively. Among all cultures, the highest $\mu_{max}$ d$^{-1}$ was in C1.

In the A culture group, the cell abundance varied from 15.45 to 25.93×10$^5$ cells mL$^{-1}$ with the highest in A3, followed by A2 and A1 (FIG. 1).

In the B group, the cell abundance varied from 18.90 to 32.97×10$^5$ cells mL$^{-1}$, and the highest was in B3, followed by B2 and B1 (FIG. 2).

Similarly, in the C group, the cell abundance varied from 23.98 to 40.92×10$^5$ cells mL$^{-1}$ with the highest in C3, followed by C2 and C1 (FIG. 3). However, among all nine cultures, C3 had the highest cell abundance of *Haematococcus* sp. KAU-01. Biomass production of *Haematococcus* sp. KAU-01 showed similar pattern as growth curve pattern of cell abundance.

Figure 4:
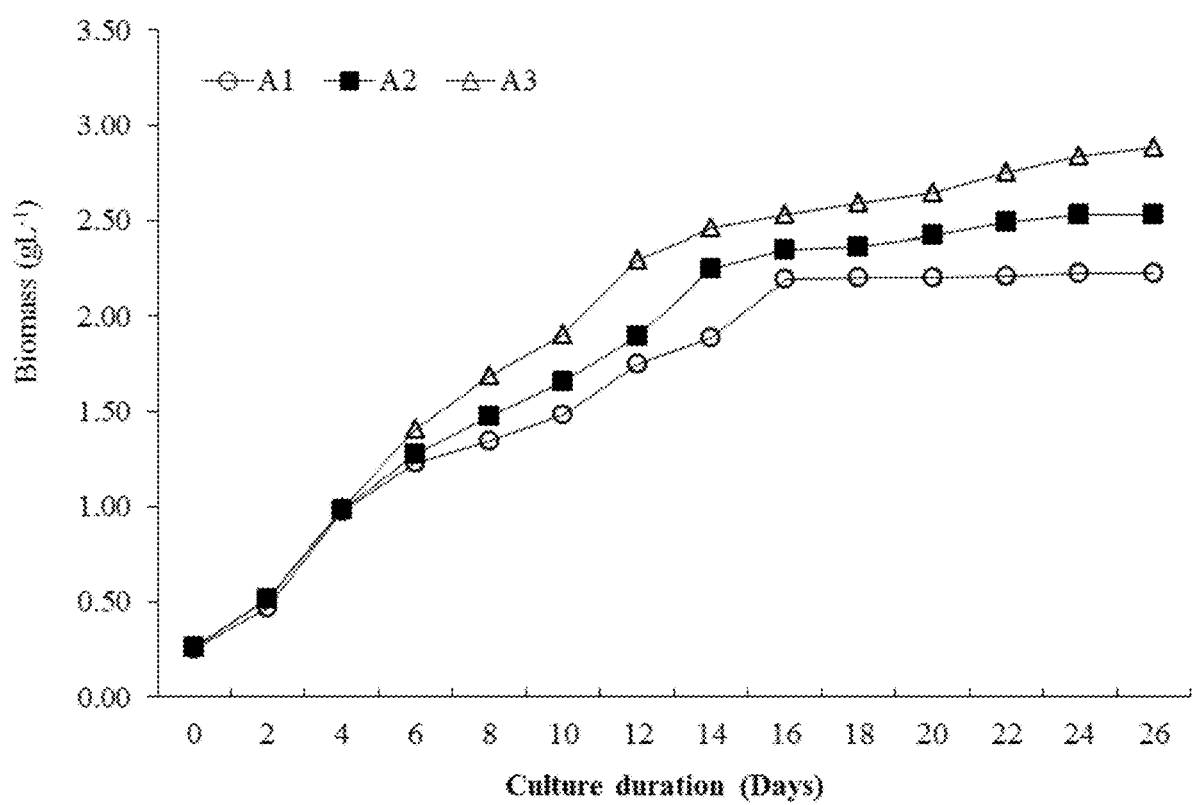
FIG. 4. Variation of biomass ($gL^{-1}$) production of *Haematococcus* sp. KAU cultured in AAHKAU medium in A culture group.

Biomass production was found to be varied from 2.19 to 2.89 gL$^{-1}$ and the highest was in A3, followed by A2 and A1 as shown by FIG. 4.

Figure 5:
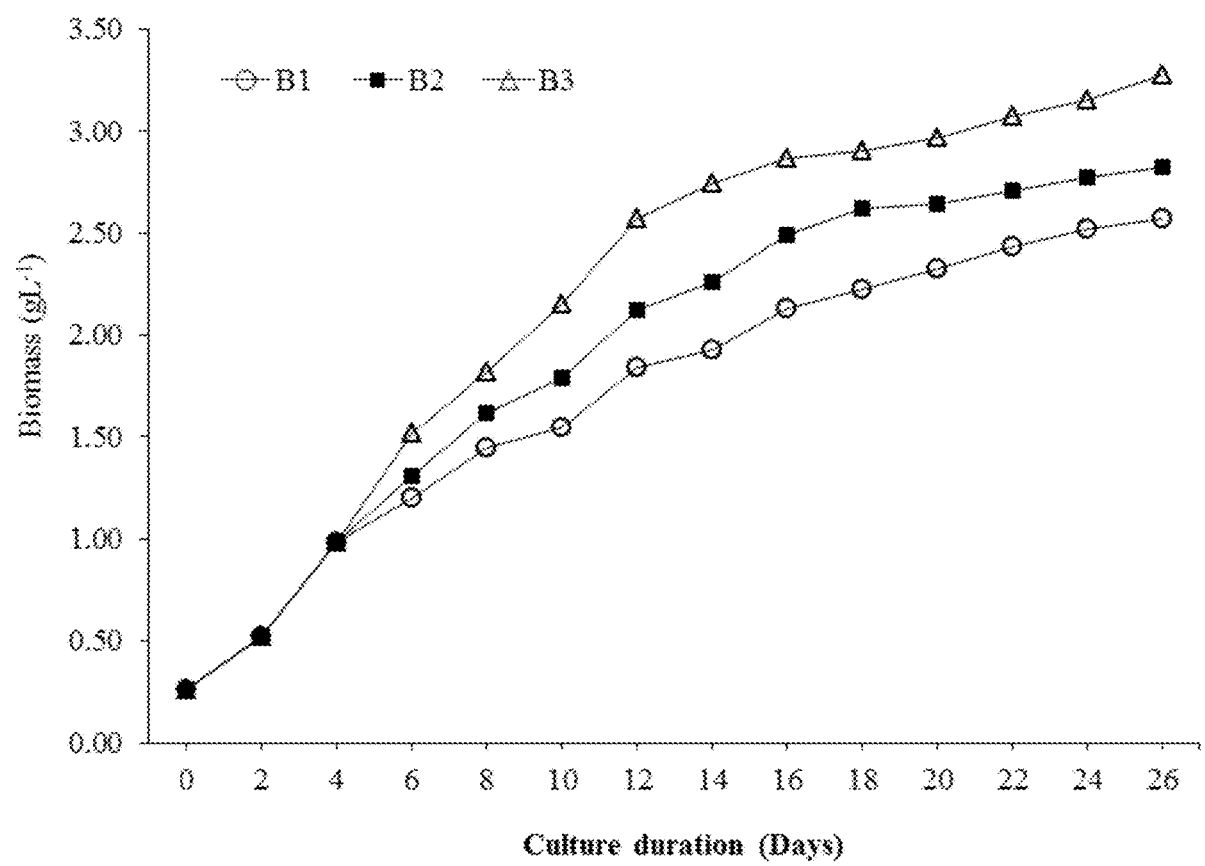
FIG. 5. Variation of biomass ($gL^{-1}$) production of *Haematococcus* sp. KAU cultured in AAHKAU medium in B culture group.

In the B group, the highest biomass production was 3.28 gL$^{-1}$ in B3 culture, followed by B2 (2.83 gL$^{-1}$) and B1 (2.57 gL$^{-1}$) as shown by FIG. 5.

Figure 6:
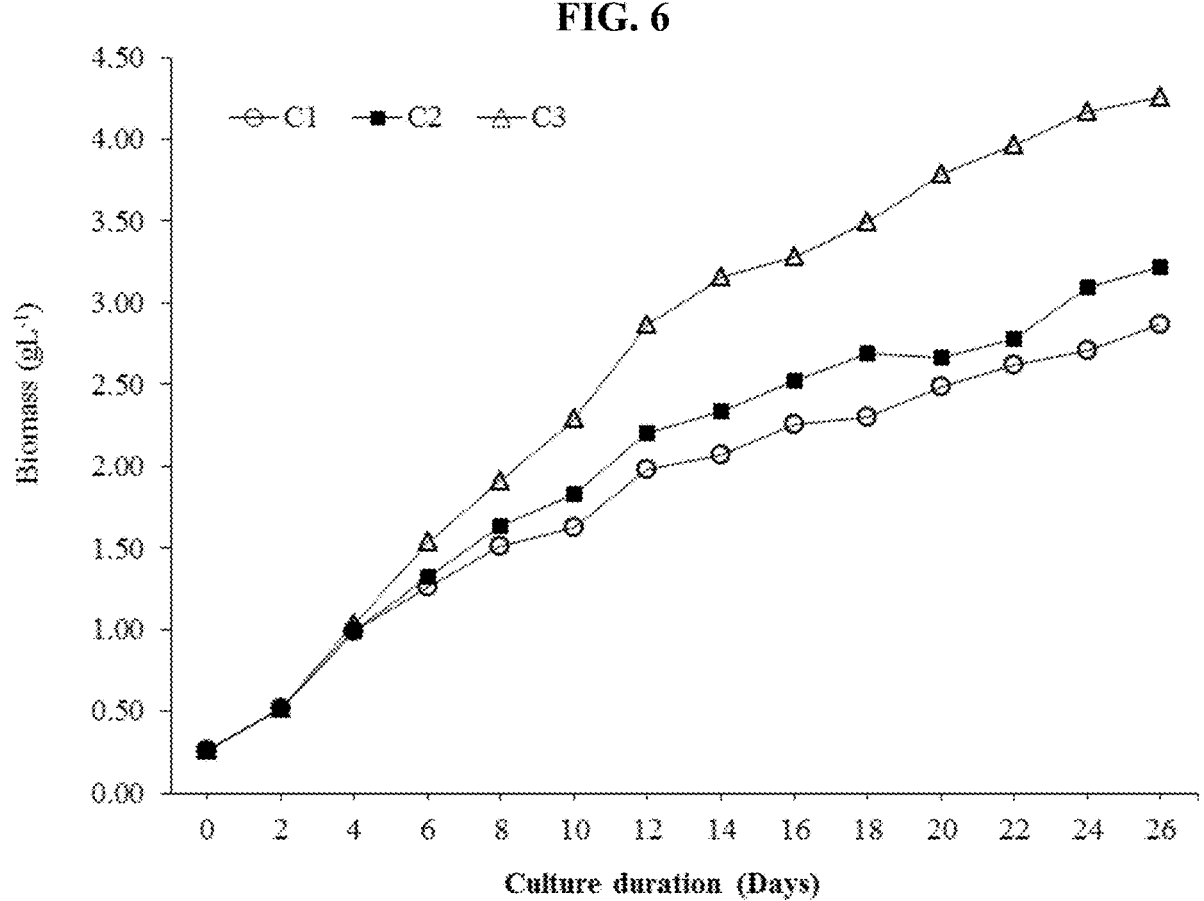
FIG. 6. Variation of biomass ($gL^{-1}$) production of *Haematococcus* sp. KAU cultured in AAHKAU medium in C culture group.

Similarly, in C group, the biomass production varied from 2.89 to 4.26 gL$^{-1}$ and the highest biomass production was found in C3 among C culture group (FIG. 6). However, the highest biomass production was found in C3 culture among the three culture groups.

Increased biomass production of B1, B2 and B3 of B group was 0.35, 0.30 and 0.90 gL$^{-1}$ higher than that the biomass production of A1, A2 and A3, respectively. The percentage calculation revealed that the biomass production of B1, B2 and B3 was 15.63, 11.68 and 37.90% more than that the biomass production of A1, A2 and A3, respectively.

Similarly, biomass production of C1, C2 and C3 group was 0.65, 0.69 and 1.89 gL$^{-1}$ higher than that the biomass production of A1, A2 and A3, respectively. A percentage calculation revealed that the biomass production of C1, C2 and C3 was 29.03, 27.32 and 79.97% more than that the biomass production of A1, A2 and A3, respectively.

In medium replacement cultures, the increased biomass production was 0.34 and 1.34 gL$^{-1}$ higher in B3 and C3 than that of the biomass production of A3, and it showed 11.71 and 45.79% high in B3 and C in comparison with A3; see Table 6 which shows the effects of culturing in the presence of air (A), CO$_2$ (B), or combustion gas mixture (C).

TABLE 6

Comparison of biomass yields (g/L) for *Haematococcus* sp. KAU-01 under conditions A (air), B (CO$_2$) and C (combustion gas mixture).

| Increased in 'B' compared to 'A' | | Increased in 'C' compared to 'A' | | | Increased in 'C' compared to 'B' | | | Increased biomass in medium replacement cultures A3, B3 and C3 | | |
|---|---|---|---|---|---|---|---|---|---|---|
| B-Cul | gL$^{-1}$ | % | C-Cul | gL$^{-1}$ | % | C-Cul | gL$^{-1}$ | % | | gL$^{-1}$ | % |
| B1 | 0.35 | 15.63 | C1 | 0.65 | 29.03 | C1 | 0.30 | 11.59 | | | |
| B2 | 0.30 | 11.68 | C2 | 0.69 | 27.32 | C2 | 0.40 | 14.00 | B3-A3 | 0.34 | 11.71 |
| B3 | 0.90 | 37.90 | C3 | 1.89 | 79.97 | C3 | 1.30 | 39.59 | C3-A3 | 1.34 | 45.79 |

TABLE 7

Difference of biomass production gram per liter (gL$^{-1}$) and percentage (%) during the culture of *Haematococcus* sp. KAU-01 under different culture conditions A1, A2 or A3; B1, B2 or B3; or C1, C2 and C3.

| | Difference of Biomass production (gL$^{-1}$) | Difference of Biomass production in percentage (%) | |
|---|---|---|---|
| Different Cultures | gL$^{-1}$ | Percent calculation | % |
| (A2-A1) | 0.31 | {(A2 − A1)/A1} × 100 | 13.77 |
| (A3-A1) | 0.66 | {(A3 − A1)/A1} × 100 | 29.82 |
| (A3-A2) | 0.36 | {(A3 − A2)/A2} × 100 | 14.10 |
| (B2-B1) | 0.25 | {(B2 − B1)/B1} × 100 | 9.89 |
| (B3-B1) | 0.71 | {(B3 − B1)/A1} × 100 | 27.50 |
| (B3-B2) | 0.45 | {(B3 − B2)/B2} × 100 | 16.02 |
| (C2-C1) | 0.35 | {(C2 − C1)/C1} × 100 | 12.27 |

TABLE 7-continued

Difference of biomass production gram per liter (gL$^{-1}$) and percentage (%) during the culture of Haematococcus sp. KAU-01 under different culture conditions A1, A2 or A3; B1, B2 or B3; or C1, C2 and C3.

| Different Cultures | Difference of Biomass production (gL$^{-1}$) gL$^{-1}$ | Difference of Biomass production in percentage (%) Percent calculation | % |
|---|---|---|---|
| (C3-C1) | 1.17 | {(C3 − C1)/C1} × 100 | 59.49 |
| (C3-C2) | 1.35 | {(C3 − C2)/C1} × 100 | 42.06 |

Table 7 shows the difference of biomass production gram per liter (gL$^{-1}$) and percentage (%) within each of the A, B and C groups thus showing the effects of different culture conditions 1, 2 or 3 on biomass production. Increased biomass production was observed in A2 and A3 which was 0.31 and 0.66 gL$^{-1}$, and it was 13.77 and 29.82% when compared with the biomass production of A1. In A3, the biomass production was 0.36 gL$^{-1}$ and 14.10% higher than that of the biomass production of A2. Similarly, in B2 and B3 the biomass production was 0.71 and 0.45 gL$^{-1}$ more in comparison with the biomass production of B1, and it was 9.89 and 27.50% than that of B1. Biomass production of B3 was 0.45 gL$^{-1}$ and 16.02% than that of the biomass production of B2.

In the C culture group, the biomass production 1.17 and 1.35 gL$^{-1}$ was higher in C2 and C3, respectively, in comparison with the biomass of C1, and it was 12.27 and 59.49% when compared with the biomass production of C1. Similarly, biomass production in C3 was 1.35 gL$^{-1}$ than that of the biomass production of C2, and it was 42.06% higher when compared with the biomass production of C2; see Table 7.

Effects of Replacement of Culture Liquids.

Figure 7:
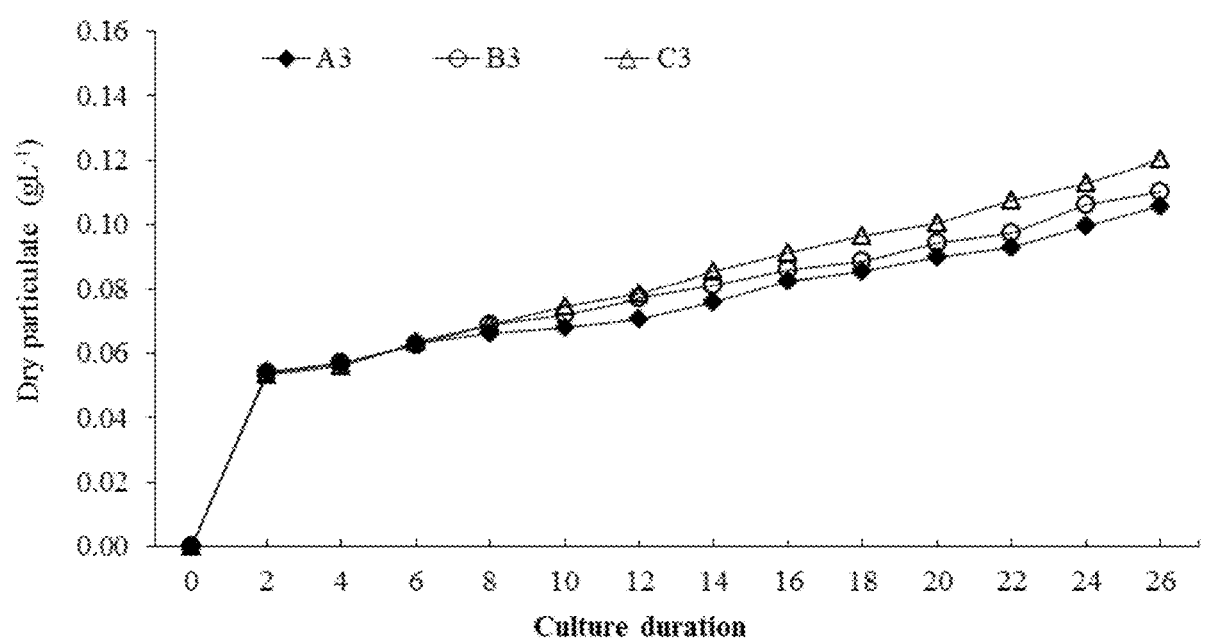
FIG. 7. Amount of dry particulate matter (cellular debris) from broken cells and cell walls during culture of *Haematococcus* sp. KAU in culture subgroups A3, B3 and C3 in which 20% of culture medium was replaced on alternate days after day 4 of culture.
Figure 11A:
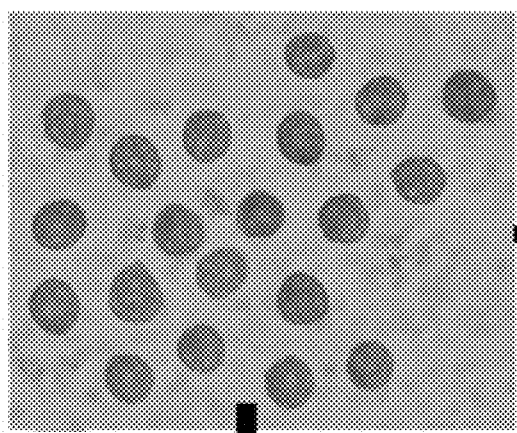
FIG. 11A depicts flagellated cells of *Haematococcus* sp. KAU-01.
Figure 11B:
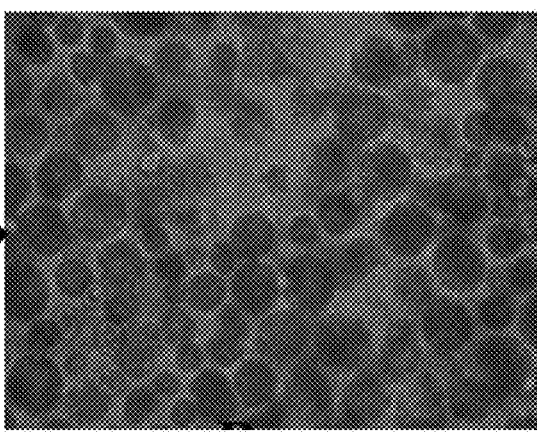
FIG. 11B shows cell walls broken or lysed due to lack of Ca-salts.
Figure 11C:
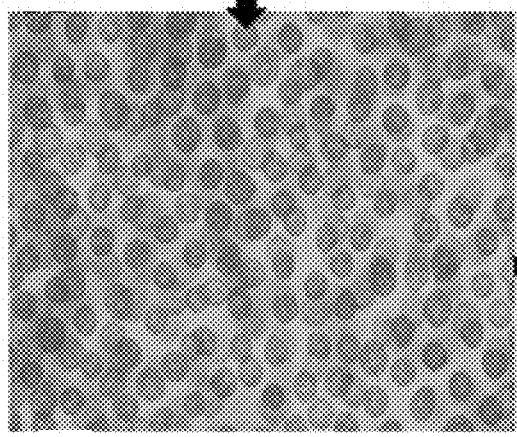
FIG. 11C shows cells without breaking of cell wall after gradually increasing Ca-salt concentration to 40 $mgL^{-1}$.
Figure 11D:
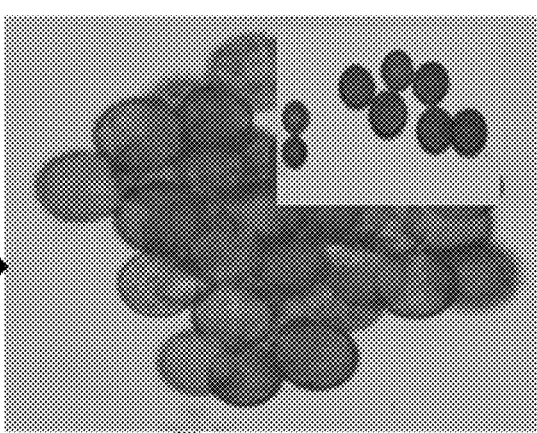
FIG. 11D depicts red cysts without lysis of cell.

The effects of replacement of liquid in the culture to reduce concentrations of cell debris, such as broken cells or cell walls, which can act as autoinhibitors of growth, were investigated. Soon after replacement, the culture medium, the discharged old culture medium was filtered following the same methods used to estimate cell biomass. The concentration of debris was 0.106, 0.110 and 0.120 gL$^{-1}$ in A3, B3 and C3, respectively, at the end of the study; FIG. 7.

Cultures of Haematococcus sp. KAU-a1 made using batch, fed batch, and culture medium replacement were grown with normal aeration, CO$_2$ and mixture gases supplying in certain interval along with normal aeration to maximize cell productivity and ultimately to obtain higher biomass production.

In all culture conditions Haematococcus sp. KAU-01 grew well but produced different cell abundances and quantities of biomass. The increasing of cell abundance was arrested soon after stationary phase when above 90% free moving cells turned into cysts or palmella.

In batch cultures having only normal aeration and/or CO$_2$ and gas mixtures supplied along with normal aeration cultures, cysts were observed earlier than in fed batch cultures and in culture medium replacement cultures.

In batch culture with normal aeration (A1) and with supply of CO$_2$ (B1) and mixture gases (C1), the cyst formation observed on 16th and 20$^{th}$ day of culture, respectively.

In fed batch culture with normal aeration (A2) and with supply of CO$_2$ (B2) and mixture gases (C2), the cyst formation was observed on 22$^{th}$ day of culture, respectively.

In replacement culture system, the cyst formation was observed on 20, 22 and 24$^{th}$ day of culture in A3, B3 and C3, respectively.

However, in replacement of culture system, the formation of palmella or cysts took longer time with normal aeration than that of the batch and fed batch cultures. Cyst formation took longest time in C3 culture, followed by B3 culture where mixture gases and CO$_2$ were supplied along with normal after replacement of culture medium. Here, the cyst formation time was longer those reported by Kaewpintong et al. who found formation of palmella from flagellated vegetative cell after 13$^{th}$ day of cultivation in M1, F1 and Hong Kong media at high-density cultivation of vegetative cells of H. pluvialis in airlift bioreactor; Kaewpintong et al., *Photoautotrophic high-density cultivation of vegetative cells of Haematococcus pluvialis in airlift bioreactor*, BIORESOURCE TECHNOLOGY, January 2007, 98(2): 288-295.

Culture of H. pluvialis in different culture media and light intensities also showed a stationary phase between 10 to 12 days which was much lower than the inventors' culture systems; Imamoglu, E., et al. *Effect of Different Culture Media and Light Intensities on Growth of Haematococcus pluvialis*. INTERNATIONAL JOURNAL OF NATURAL AND ENGINEERING SCIENCES, 2007, 3, 05-09. Medium replacement cultures supplied with CO$_2$ and gas mixtures showed almost double capacity to form cysts than that of cyst formation than in the culture study of Kaewpintong et al., supra and Imamoglu, E., et al., supra.

Cell growth generally occurs when vegetative cells are flagellated. In palmella (cysts) the cells convert to an inactive form and cease further cell division. These results show that culture medium and conditions were quite suitable and facilitated cell division for a long time, thus ultimately increasing of cell abundance and biomass production. Moreover, it showed that replacement of culture medium with supplying of CO$_2$ and mixture gases along with normal aeration provided a higher efficiency to facilitate more cell division by providing suitable conditions for long time than in batch and fed batch culture systems.

Cell abundance and Biomass production. The inventors sought to acquire biological information, such as growth characteristics of Haematococcus sp. KAU-01 to discover mass culture to construct a high-density mass culture system. The $u_{max}$ d$^{-1}$ was significantly (p<0.05) higher in 'C' culture group than that of the $u_{max}$ d$^{-1}$ of 'A' and 'B' culture group, except for 'A1'' culture, where the maximum cell growth and stationary phase were appeared about a week before than all other cultures. The $u_{max}$ d$^{-1}$ in all cultures of this study was low in comparison with the study of Kaewpintong et al., supra who found $u_{max}$ d$^{-1}$ of 0.21 d$^{-1}$ in F1 culture medium on 8$^{th}$ day of culture. Tjahj ono et al. found the maximum specific growth rate of H. pluvialis was about 0.25 d$^{-1}$ using basal growth medium grown in mixotrophic condition with sodium acetate as a carbon source on 3$^{rd}$ day of culture; Tjahjono et al., *Hyper-accumulation of astaxanthin in a green alga Haematococcus pluvialis at elevated temperatures*, BIOTECHNOLOGY LETTERS. 1994, 16:133-138.

The $\mu_{max}$d$^{-1}$ can vary from culture to culture as well as initial cell abundance and occurrence of maximum cells abundance. However, the cell abundance was significantly higher (p<0.05) in all medium replacement cultures, followed by fed batch culture and batch culture. In batch culture with supplying of normal aeration, periodic supply of CO$_2$ and mixture gases along with normal aeration, the maximum cell abundance was 15.54×10$^5$, 18.90×10$^5$ and 23.98×10$^5$ cells mL$^{-1}$ in A1, B1 and C1 cultures, respectively (FIGS. 1, 2 & 3). Within batch culture, supply of mixture gases, $CO_2$ and normal aeration also showed significant ($p<0.05$) difference in cell abundance occurrence.

The cells abundance of batch cultures of normal aeration and supplying mixture gases, $CO_2$ along with normal aeration showed almost two to three folds higher than that of the results of obtained by Imamoglu et al., supra who reported that the maximum cell abundance occurred $7.75\times10^5$ and $8.10\times10^5$ cells $mL^{-1}$ in BG11 and RM culture media, respectively under the light intensity of 50 µmol photons $m^{-2}$ $s^{-1}$ and in RM medium, the recorded cell abundance was $9.50\times10^5$ cells $mL^{-1}$ when culture under 40 µmol photons $m^{-2}$ $s^{-1}$.

In fed batch cultures, the maximum cell abundance was $19.95\times10^5$, $25.17\times10^5$ and $31.50\times10^5$ cells $mL^{-1}$ in A2, B2, and C2 cultures, respectively (FIGS. 1, 2 and 3). Within fed batch cultures, the occurrence of cell abundance was also significantly different, especially cell abundance in C2 was significantly ($p<0.05$) higher than that of B2, followed by A2 culture. Kaewpintong et al. studied high-density cultivation of vegetative cells of *H. pluvialis* in airlift bioreactor with supplying $CO_2$ and attained the maximum cell abundance $46\times10^4$ and $79.5\times10^4$ cells $mL^{-1}$, which is much lower than that of the cell abundance of the batch culture disclosed herein with periodic supplying of $CO_2$ and mixture gases as well as fed batch culture with supplying of $CO_2$ and mixture gases. The cell abundance was higher in all batch cultures in comparison with the above mentioned previous study.

This is consistent with the AAHKAU medium creating favorable circumstances for the higher growth of *Haematococcus* sp. KAU-01 in batch and fed batch culture with normal aeration or with periodic supply of $CO_2$ and mixture gases along with normal aeration. Cultures supplied with mixture gases showed more cell abundance than all other cultures. Moreover, the remarkable maximum cell abundance occurrence was found in a 20% replacement culture medium. The cell abundance was $25.93\times10^5$, $32.97\times10^5$ and $40.92\times10^5$ cells $mL^{-1}$ in culture of A3, B3, and C3, respectively (FIGS. 1, 2 & 3). The cell abundance occurrence results in the medium replacement culture was much higher than those reported by Hata, N., et al., *Production of astaxanthin by Haematococcus pluvialis in a sequential heterotrophic photoautotrophic culture*. JOURNAL OF APPLIED PHYCOLOGY. 2001, 13, 395-402.

Biomass production. Biomass production was found to be high in all media replacement cultures. The $1^{st}$ highest was 4.26 $gL^{-1}$ in C3 culture where mixture gases was supplied along with normal aeration, and the $2^{nd}$ highest was in B3 culture where $CO_2$ gas was supply in same way to the medium replacement culture. This biomass production was higher in comparison with the biomass production of *H. lacustris* culture in $NH_4Cl$ enriched medium with supply of 2% $CO_2$ as bubbles, where the biomass production was 3.74 $gL^{-1}$.

Higher biomass production in $CO_2$ and mixture gases supplying cultures confirmed that $CO_2$ and mixtures gases were converted to algal biomass by increasing the components for photosynthesis.

It was also found that the biomass production in cultures supplied with mixture gases showed more biomass production than that of the biomass production by only supplying $CO_2$.

Mixture gases which are similar to flue gases (greenhouse gases) can be added as a gas or in bicarbonate form as cultivated microalgae grow too fast to be able to take sufficient flue gases from the water. Compressed air can be blended and provided for algal photosynthesis. Therefore, high valued microalgae can be grown in high cell density for $CO_2$ sequestration from flue gases, which ultimately reduces the emission of flue gases from fossil fuel-fired power plants.

These results demonstrate the remarkable growth of a commercially valuable microalgae *Haematococcus* sp. KAU-01 in newly formulated AAHKAU culture medium with normal aeration as well as in cultures having a periodic supply of $CO_2$ and/or mixture gases along with normal aeration. Superior results were obtained by replacement of culture medium to remove microalga autoinhibitors from ongoing cultures. This technology can be used for profitable, large scale biomass production while simultaneously controlling undesirable emissions of flue gases from the fossil fuel power plants.

Terminology used herein is for the purpose of describing particular embodiments only and is not intended to limit the invention.

Unless defined otherwise, all technical and scientific terms used herein have the same meaning as commonly understood by one of ordinary skill in the art to which this invention belongs. In case of conflict, the present application including the definitions will control.

Unless otherwise required by context, singular terms shall include pluralities and plural terms shall include the singular. All ranges provided within the application are inclusive of the values of the upper and lower ends of the range unless specifically indicated otherwise.

The term "and/or" as used in a phrase such as "A and/or B" herein is intended to include "A and B", "A or B", "A", and "B".

"About" means either within 10% of the stated value, or within 5% of the stated value, or in some cases within 2.5% or 1% of the stated value, or, "about" can mean rounded to the nearest significant digit.

The terms "naturally-occurring", "native", and "wild-type" refer to a form of *Haematococcus* sp. KAU- found in nature. For example, a naturally occurring or wild-type isolate of *Haematococcus* sp or a genetically or epigenetically unmodified parent strain to *Haematococcus* sp. KAU "Epigenetic modifications" are persistent and heritable changes made to the DNA, which regulate how genes are expressed, but do not affect the nucleotide sequence itself. Epigenetic modifications include DNA methylation, histone modification, and microRNA. A micro RNA (abbreviated miRNA) is a small non-coding RNA molecule (containing about 22 nucleotides) found in plants, animals and some viruses, that functions in RNA silencing and post-transcriptional regulation of gene expression regulation.

"Exogenous nucleic acid molecule", "transgene", or "exogenous gene" refers to a nucleic acid molecule or gene that has been introduced (e.g., transformed) into a cell such as into *Haematococcus* sp. KAU. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. An "endogenous" nucleic acid molecule, gene or protein is a native nucleic acid molecule, gene, or protein as it occurs in, or is naturally produced by, the host.

The term "recombinant protein" as used herein refers to a protein produced by genetic engineering regardless of whether the amino acid sequence varies from that of a wild-type protein or *Haematococcus* sp. KAU-01.

When applied to organisms, such as variants of *Haematococcus* sp. KAU-01, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for reduced gene expression or gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or Cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than *Haematococcus* sp. KAU-01 or that has a non-identical nucleic acid sequence or epigenetic form. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. Polypeptides of *Haematococcus* sp. KAU-01 include those enzymes required for carotenoid production.

As used herein carotenoids include lutein, β-carotene, violaxanthin, neoxanthin, and zeaxanthin, chlorophyll a and b and other carotenoids produced by *Haematococcus* sp. KAU- or variants thereof.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, a shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide. Thus, a modified *Haematococcus* sp. KAU-01 may express less or more of a particular mRNA, protein or other valuable product such as a carotenoid like astaxanthin.

Some aspects of the present invention include the partial, substantial, or complete attenuation, deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site-directed homologous recombination or targeted integration or mutation using a Cas/CRISPR system to knockout a particular gene of interest. In still other embodiments, targeted insertion into or mutation of a gene regulatory region using a Cas/CRISPR system, RNAi, or antisense DNA (asDNA) constructs may be used to partially, substantially, or completely silence, inactivate, or down-regulate a particular gene of interest in *Haematococcus* sp. KAU-01.

The insertions, deletions, or other modifications of certain nucleic acid molecules or particular polynucleotide sequences in *Haematococcus* sp. KAU-01 may be understood to encompass "genetic modification(s)" or "transformation(s)" such that the resulting strains of the microorganisms or host cells may be understood to be "genetically modified", "genetically engineered" or "transformed."

As used herein, "enhancing the expression" includes an increase in expression of a gene or nucleic acid molecule of interest or the activity of an enzyme in a modified *Haematococcus* sp. KAU-01 comprising one or more genetic modifications as compared to the expression or activity in a control, unmodified *Haematococcus* sp. KAU-01 without such genetic modifications.

Reference to properties or compositions that are "substantially the same" or "substantially identical" indicates minor and irrelevant deviations that are not material to the characteristics considered important in the context of the invention. In various embodiments this can mean the properties are within 10%, and preferably within 5%, within 2.5% or within 1%, of the reference value. For example, AAHKAU medium with a variation of 1% in the content of one or more ingredients could be considered substantially the same as AAHKAU medium formulation described herein.

The materials, methods, and examples are illustrative only and are not intended to be limiting. Other features and advantages of the invention will be apparent from the description and from the claims.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for producing biomass comprising culturing a Haematococcus sp. that is Haematococcus sp. KAU-01 deposited under patent depository number P0088700 in culture medium in the presence of light, wherein the light may be present intermittently, periodically or continuously;
wherein the culture medium comprises AAHKAU culture medium that contains about:
375.00 mg/L $NaNO_3$,
75.00 mg/L $KNO_3$,
25.00 mg/L $Ca(NO_3)_2$,
55.00 mg/L $Mg(NO_3)_2 \cdot 6H_2O$,
10.00 mg/L $K_2SO_4$,
45.00 mg/L $K_2HPO_4$,
40.00 mg/L $KH_2PO_4$,
23.75 mg/L $MgSO_4 \cdot 7H_2O$
1.755 mg/L urea,
65 µl/L $HNO_3$,
15 µl/L $H_3PO_4$;
3.50 mg/L $FeCl_3 \cdot 6H_2O$,
1.00 mg/L $H_3BO_3$,
0.25 mg/L $Co(NO_3)_2 \cdot 6H_2O$,
0.10 mg/L $K_2Cr_2O_7$,
0.10 mg/L $CuSO_4 \cdot 5H_2O$,
0.25 mg/L $MnSO_4 \cdot H_2O$,
0.75 mg/L $ZnSO_4 \cdot 6H_2O$,
0.25 mg/L $(NH_4)_6Mo_7O_{24} \cdot 4H_2O$,
1.00 mg/L $Na_e$-EDTA,
1.00 µl/L HCl; and
water;
wherein one or more of said concentrations may vary by up to ±10%; and
wherein the culture medium further comprises at least one material comprising carbon dioxide obtained by combustion of a fuel.

2. The method of claim 1, wherein the light is natural, reflected, filtered, focused, or concentrated sunlight.

3. The method of claim 1, wherein at least one material is incorporated into a gas, liquid or solid prior to incorporating it into the culture medium.

4. The method of claim 1, wherein the at least one material is obtained by combustion of coal.

5. The method of claim 1, wherein the at least one material is obtained by combustion of coal and is obtained from a flue gas scrubber.

6. The method of claim 1, wherein the at least one material comprises carbon monoxide.

7. The method of claim 1, wherein the at least one material comprises a nitrogen oxide.

8. The method of claim 1, wherein the at least one material comprises a sulfur oxide.

9. The method of claim 1, wherein the at least one material is a volatile organic compound.

10. The method of claim 1, further comprising reducing an amount of at least one heavy metal present in the material prior to incorporating it into the culture medium.

11. The method of claim 1, wherein said culturing comprises fed-batch culturing.

12. The method of claim 1, wherein said culturing comprises fed-batch culturing and wherein each feeding comprises replacing from 5 to 50% of a spent culture medium with fresh culture medium and, optionally, adjusting the pH to range from 6 to 8.

13. The method of claim 1, wherein the AAHKAU medium contains a concentration of elemental Ca ranging from 2.41 to 7.24 mg/L and/or a concentration of elemental Mg ranging from 3.23 to 9.69 mg/L.

14. The method of claim 1, further comprising recovering the biomass by filtration, centrifugation and/or sedimentation.

* * * * *